(12) United States Patent
Struble et al.

(10) Patent No.: US 6,477,420 B1
(45) Date of Patent: Nov. 5, 2002

(54) CONTROL OF PACING RATE IN MODE SWITCHING IMPLANTABLE MEDICAL DEVICES

(75) Inventors: Chester L. Struble, Eijsden (NL); David Dunham, Brackley (GB)

(73) Assignee: Medtronic, Inc, Minneapolis, MN (US)

( * ) Notice: Subject to any disclaimer, the term of this patent is extended or adjusted under 35 U.S.C. 154(b) by 0 days.

(21) Appl. No.: 09/842,879

(22) Filed: Apr. 27, 2001

(51) Int. Cl.[7] ............................................. A61N 1/362
(52) U.S. Cl. ...................................................... 607/14
(58) Field of Search ................................. 607/9, 14, 5

(56) References Cited

U.S. PATENT DOCUMENTS

| | | |
|---|---|---|
| 4,316,472 A | 2/1982 | Mirowski et al. |
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson |
| 4,556,063 A | 12/1985 | Thompson et al. |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallock |
| 4,800,883 A | 1/1989 | Winstrom |
| 4,821,723 A | 4/1989 | Baker, Jr. et al. |
| 4,830,006 A | 5/1989 | Haluska et al. |
| 4,880,005 A | 11/1989 | Pless et al. |
| 4,928,688 A | 5/1990 | Mower |
| 4,932,406 A | 6/1990 | Berkovits |
| 4,944,298 A | 7/1990 | Sholder |
| 4,949,719 A | 8/1990 | Pless et al. |
| 4,953,551 A | 9/1990 | Mehra et al. |
| 5,099,838 A | 3/1992 | Bardy |
| 5,117,824 A | 6/1992 | Keimel et al. |
| 5,131,388 A | 7/1992 | Pless |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,269,298 A | 12/1993 | Adams et al. |
| 5,292,340 A | 3/1994 | Crosby et al. |
| 5,312,453 A | 5/1994 | Shelton et al. |
| 5,314,430 A | 5/1994 | Bardy |
| 5,318,594 A | 6/1994 | Limousin et al. |
| 5,354,316 A | 10/1994 | Keimel |
| 5,354,319 A | 10/1994 | Wyborny et al. |
| 5,545,186 A | 8/1996 | Olson et al. |
| 5,690,686 A | 11/1997 | Min et al. |
| 5,792,203 A | 8/1998 | Schroeppel |
| 5,800,465 A | 9/1998 | Thompson et al. |
| 5,893,882 A | 4/1999 | Peterson et al. |
| 5,902,324 A | 5/1999 | Thompson et al. |
| 6,070,101 A | 5/2000 | Struble et al. |
| 6,081,748 A | 6/2000 | Struble et al. |

FOREIGN PATENT DOCUMENTS

WO    WO 92/18198    10/1992

OTHER PUBLICATIONS

Arzbaecher et al., "Automatic Tachycardia Recognition," *PACE*, 541–547 (May–Jun. 1984).

Olson et al., "Onset and Stability for Ventricular Tachyarrhythmia Detection in an Implantable Pacer–Cardioverter–Defibrillator," *Computers in Cardiology*, IEEE Computer Society Press, 167–170 (Oct. 7–10, 1986).

*Primary Examiner*—Scott M. Getzow
(74) *Attorney, Agent, or Firm*—Thomas F. Woods; Eric R. Waldkoette; Tom G. Berry

(57) ABSTRACT

An implantable medical device and method of pacing provide for switching from a first pacing mode to second pacing mode upon detection of a period of accelerated atrial arrhythmia. Generally, the second pacing mode has an associated predetermined lower pacing rate. At least initially, upon switching from the first pacing mode to the second pacing mode, the predetermined lower pacing rate is adjusted to an elevated adjusted lower rate. Further, this elevated adjusted lower rate may then be decelerated towards a programmed basic pacing rate during a deceleration period. Generally, the programmed basic pacing rate is elevated relative to the predetermined lower pacing rate.

40 Claims, 12 Drawing Sheets

CONTROL OF PACING RATE IN MODE SWITCHING IMPLANTABLE MEDICAL DEVICES

FIELD OF THE INVENTION

The present invention relates generally to implantable medical devices and methods for cardiac stimulation. More particularly, the present invention pertains to implantable medical devices and methods that employ mode switching in cardiac stimulation.

BACKGROUND OF THE INVENTION

Generally, in the human heart, the sinus (or sinoatrial (SA) node typically located near the junction of the superior vena cava and the right atrium) constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrio-ventricular (AV) node, and via a conduction system comprising the bundle of His, or common bundle, the right and left bundle branches, and the Purkinje fibers. The transmitted impulse causes the ventricles to contract with the right ventricle pumping unoxygenated blood through the pulmonary artery to the lungs and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

The above action is repeated in a rhythmic cardiac cycle in which the atrial and ventricular chambers alternately contract and pump, and then relax and fill. One-way valves, between the atrial and ventricular chambers on the right and left sides of the heart, and at the exits of the right and left ventricles, prevent backflow of the blood as it moves through the heart and the circulatory system. This sinus node is spontaneously rhythmic, and the cardiac rhythm it generates is termed sinus rhythm. This capacity to produce spontaneous cardiac impulse is called rhythmicity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. A pacemaker is a medical device which delivers electrical pulses to an electrode that is implanted adjacent to or in the patient's heart to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart.

Implantable pacemakers are typically designed to operate using various different response methodologies, such as, for example, nonsynchronous or asynchronous (fixed rate), inhibited (stimulus generated in the absence of a specified cardiac activity), or triggered (stimulus delivered in response to a specific hemodynamic parameter). Generally, inhibited and triggered pacemakers may be grouped as "demand"-type pacemakers, in which a pacing pulse is only generated when demanded by the heart. To determine when pacing is required by the pacemaker, demand pacemakers may sense various conditions such as heart rate, physical exertion, temperature, and the like. Moreover, pacemaker implementations range from the simple fixed rate, single chamber device that provides pacing with no sensing function, to highly complex models that provide fully-automatic dual chamber pacing and sensing functions. For example, such multiple chamber pacemakers are described in U.S. Pat. No. 4,928,688 to Mower entitled "Method and Apparatus for Treating Hemodynamic Dysfunction," issued May 29, 1990; U.S. Pat. No. 5,792,203 to Schroeppel entitled "Universal Programmable Cardiac Stimulation Device," issued Aug. 11 , 1998; U.S. Pat. No. 5,893,882 to Peterson et al. entitled "Method and Apparatus for Diagnosis and Treatment of Arrhythmias," issued Apr. 13, 1999; and U.S. Pat. No. 6,081,748 to Struble et al. entitled "Multiple Channel, Sequential Cardiac Pacing Systems," issued Jun. 27, 2000.

Because of the large number of options available for pacer operation, an industry convention has been established whereby specific pacer configurations are identified according to a code comprising multiple letters (generally, three to four letters, although a fifth coded position may also be used). The most common configuration codes comprise either three or four letters, as shown in Table I below. For simplicity, the fifth coded position is omitted. Each code can be interpreted as follows:

TABLE I

| | Code Position | | | |
|---|---|---|---|---|
| | 1 | 2 | 3 | 4 |
| function identified options available | chamber paced<br>0 - none<br>A - atrium<br>V - ventricle<br>D - dual<br>(A + V) | chamber sensed<br>0 - none<br>A - atrium<br>V - ventricle<br>D - dual<br>(A + V) | response to sensing<br>0 - none<br>T - triggered<br>I - inhibited<br>D - dual<br>(T + I) | programmability rate modulation<br>0 - none<br>P - programmable<br>M - multi-programmable<br>C - communicating<br>R - rate modulating |

For example, a DDD pacer paces either chamber (atrium or ventricle) and senses in either chamber. Thus, a pacer in DDD mode, may pace the ventricle in response to electrical activity sensed in the atrium. A VVI pacer paces and senses in the ventricle, but its pacing is inhibited by spontaneous electrical activity of the ventricle, also referred to as intrinsic ventricular activity (i.e., the ventricle paces itself naturally). In VVIR mode, ventricle pacing is similarly inhibited upon determining that the ventricle is naturally contracting. With the VVIR mode, the pacer's pacing rate, however, in the absence of naturally occurring pacing, is modulated by the physical activity level of the patient. Pacers commonly include accelerometers to provide an indication of the patient's level of physical activity.

As illustrated in the table above, it may be desirable to sense in one cardiac chamber (e.g., detect electrical activity represented of contraction of the chamber and referred to as a "sensed event") and, in response, pace (referred to as a "paced event") in the same or different chamber. It also may be desirable to pace at two electrode locations following a sensed event. For example, patients with abnormally fast atrial rhythms (referred to as atrial tachyarrhythmias) are often treated with pacemakers that include an electrode in each of the two atrial chambers and a third electrode in the right ventricle. Both atrial chambers usually are paced following a sensed event in either chamber. Various pacemaker protocols may be used.

Further, for example, some patients, like heart failure patients, are often treated with bi-ventricular pacemakers that include an electrode in each of the two ventricular chambers, and also possible a third electrode in the right atrium. Both ventricular chambers usually are paced following a sensed or paced atrial event.

In the context of dual chamber pacing, a variety of mode switching features have been developed which detect an excessively rapid atrial rhythm and in response cause the pacemaker to switch from an atrial synchronized pacing mode such as DDD to a nonsynchronized mode such as VVI or DDI. Such mode switching features are disclosed in U.S. Pat. No. 5,144,949 to Olson entitled "Dual Chamber Rate Responsive Pacemaker With Automatic Mode Switching," issued Sep. 8, 1992; U.S. Pat. No. 5,318,594 to Limousin et al. entitled "DDD Type Cardiac Pacemaker Having Automatic Operating Mode Switching," issued Jun. 7, 1994; U.S. Pat. No. 4,944,298 to Sholder entitled "Atrial Rate Based Programmable Pacemaker With Automatic Mode Switching Means," issued Jul. 31, 1990; U.S. Pat. No. 4,932,406 to Berkovits entitled "Dual Chamber Rate Responsive Pacemaker," issued Jun. 12, 1990; and U.S. Pat. No. 5,292,340 to Crosby et al. entitled "Physiologically-Calibrated Rate Adaptive, Dual Chamber Pacemaker," issued Mar. 8, 1994. In such devices, the primary purpose of the mode switch is to prevent the pacemaker from tracking a non-physiologic atrial rate.

Generally, mode switching is generally in most dual chamber pacemakers. Such mode switching typically changes the mode of pacing therapy during periods of accelerated atrial arrhythmias such as, for example, SVT (supra ventricular tachycardia), PAF (paroxysmal atrial flutter), and AF (atrial fibrillation). For example, mode switching may change the dual chamber pacing mode from DDD to DDI, DDDR to DDIR, VDD to VVI, or VDDR to VVIR.

During such episodes of mode switching due to periods of accelerated atrial arrhythmias such as SVT/PAF/AF, the pacemaker will revert to a lower rate (LR) of pacing (or a sensor-driven pacing rate or frequency in rate modulating operating modes such as DDIR or VVIR). In many cases, the LR is programmed below that of the intrinsic rate of the patient's sinus rhythm. For example, the LR may be 60 ppm when the sinus rhythm of the patient is 70 bpm. As such, with regard to patients with ventricular dysfunction (e.g., heart failure), because such patients are inactive due to their severe conditions, the heart rate may be paced at an insufficient low pacing rate, i.e., LR.

Therefore, such mode switching may result in insufficient pacing rate and cardiac output. For example, during mode switching periods, as described above, the pacemaker may pace the heart at the LR in a mode such as DDI(R) or VVI(R). DDIR behaves much like VVIR in the case of atrial tachyarrhythmias. This pacing LR is typically too slow to guarantee sufficient cardiac output in heart failure patients.

In addition to the potential lower cardiac output due to pacing at the LR, reduced cardiac output may also occur due to the atrial arrhythmia and loss of atrial contribution to ventricular filling. For example, all atrial contribution (e.g., "atrial kick") to ventricular filling may be lost during atrial arrhythmia. As such, stroke volume becomes reduced, e.g., reduced by 20–25%, because cardiac output=(heart rate) (stroke volume). Due to the above, such reduced cardiac output may be inadequate for the patient.

Further, during periods of accelerated atrial arrhythmias (e.g., SVT/PAF/AF), AV conduction often occurs irregularly. Such irregular AV conduction may result in irregular intrinsic ventricular response (e.g., ventricular response rates of 100 bpm due to the attempt of the ventricular chamber to respond intrinsically to the accelerated arrhythmias to the LR of 60 ppm when no intrinsic ventricular response is detected and the ventricular chamber is paced at LR).

Yet further, in bi-ventricular pacing for heart failure patients, continuous pacing therapy should be maintained. During mode switching, there may be a loss of such continuous bi-ventricular pacing therapy.

Table II below lists U.S. Patents relating to multiple chamber pacing apparatus and mode switching techniques and methods.

TABLE II

| U.S. Pat. No. | Inventor | Issue Date |
| --- | --- | --- |
| 4,928,688 | Mower | 29 May 1990 |
| 4,932,406 | Berkovits | 12 June 1990 |
| 4,944,298 | Sholder | 31 July 1990 |
| 5,144,949 | Olson | 8 September 1992 |
| 5,292,340 | Crosby et al. | 8 March 1994 |
| 5,318,594 | Limousin et al. | 7 June 1994 |
| 5,792,203 | Schroeppel | 11 August 1998 |
| 5,893,882 | Peterson et al. | 13 April 1999 |
| 5,902,324 | Thompson et al. | 11 May 1999 |
| 6,070,101 | Struble et al. | 30 May 2000 |
| 6,081,748 | Struble et al. | 27 June 2000 |

All references listed in Table II, and elsewhere herein, are incorporated by reference in their respective entireties. As those of ordinary skill in the art will appreciate readily upon reading the Summary of the Invention, Detailed Description of the Embodiments, and claims set forth below, at least some of the devices and methods disclosed in the references of Table II and elsewhere herein may be modified advantageously by using the teachings of the present invention. However, the listing of any such references in Table II, or elsewhere herein, is by no means an indication that such references are prior art to the present invention.

SUMMARY OF THE INVENTION

The present invention has certain objects. That is, various embodiments of the present invention provide solutions to one or more problems existing in the prior art with respect to implantable medical device pacing techniques and, in particular, mode switching used in conjunction with such pacing techniques. One of such problems involves the provision of insufficient pacing rate and cardiac output during mode switching periods. Further, for example, other problems involve the occurrence of irregular AV conduction during accelerated atrial arrhythmias and mode switching periods that often result in irregular intrinsic ventricular response. In addition, for example, in bi-ventricular pacing for heart failure patients, during mode switching periods upon detection of accelerated atrial arrhythmias, pacing therapy may not be continuous.

In comparison to known mode switching techniques, various embodiments of the present invention may provide one or more of the following advantages. For example, the highest level of continued ventricular therapy, e.g., bi-ventricular pacing therapy, during mode switching periods due to accelerated atrial arrhythmias, is ensured. Further, an elevated pacing rate counteracts the absence of atrial contribution to ventricular filling in patients during periods of atrial arrhythmias. Yet further, the present invention provides for interaction in the mode switching period with a rate response activity sensor indicated rate to provide for more appropriate pacing rates when a patient is undertaking greater activity, e.g., exercise. In general, by making adjustments to lower rate pacing during mode switching, such that an elevated compensatory rate is provided, the present invention provides the advantage of providing sufficient cardiac output during episodes of accelerated atrial arrhythmias.

Some embodiments of the present invention include one or more of the following features: detection of a period of accelerated atrial arrhythmias; switching from a first pacing mode to a second pacing mode upon detection of a period of accelerated atrial arrhythmias; provision of a first pacing mode (e.g., DDD, DDDR, VDD, or VDDR pacing mode) that paces at least one ventricle based on sensed atrial activity and a second pacing mode (e.g., DDI, DDIR, VVI, or VVIR pacing mode) that paces the at least one ventricle based on sensed ventricular activity at a predetermined lower rate with such pacing inhibited based on intrinsic ventricular activity; adjusting a lower rate to an elevated adjusted lower rate upon switching from a first pacing mode to a second pacing mode such that pacing of the at least one ventricle is not inhibited based on intrinsic ventricular activity; adjusting a lower rate to an elevated adjusted lower rate based on R-R intervals measured during a ventricular response detection time window associated with mode switching; adjusting a lower rate based on at least the fastest R-R interval measured during a ventricular response detection time window; limiting the elevated adjusted lower rate based on a programmed maximum pacing rate; taking into consideration an activity sensor indicated pacing rate when determining an appropriate rate; decelerating from an elevated adjusted lower rate towards a predetermined basic pacing rate that is as fast or faster than the predetermined or programmed lower rate; monitoring ventricular activity during the deceleration period and readjusting the elevated adjusted lower rate upon detection of an intrinsic ventricular event and further decelerating the readjusted elevated lower rate during a reinitiated deceleration period; and continuing deceleration to a predetermined pacing rate if no intrinsic ventricular events are detected and thereafter continuing to use a predetermined basic pacing rate until either an intrinsic ventricular event is detected and a readjusted elevated lower rate is reset for deceleration or mode of operation is switched back.

Still further, some embodiments of the present invention include one or more of the following features: pacing generator circuitry operable to generate pacing pulses at one or more pacing rates during at least first and second pacing modes; a first pacing mode that paces at least one ventricle based on sensed atrial activity (e.g., DDD, DDR, VDD, or VDDR); a second pacing mode that paces the at least one ventricle based on sensed ventricular activity at a predetermined lower rate (e.g., a programmed rate) with such pacing inhibited based on intrinsic ventricular activity (e.g., DDI, DDIR, VVI, or VVIR pacing mode); sensing circuitry operable to sense atrial and ventricular activity; a pacing controller operable to switch from a first pacing mode to a second pacing mode upon detection of a period of accelerated atrial arrhythmia based on information from sensing circuitry; a pacing controller operable to at least initially upon switching from a first pacing mode to a second pacing mode adjust a predetermined lower rate to an elevated adjusted lower rate such that pacing of at least one ventricle is not inhibited based on detected intrinsic ventricular activity; a pacing controller that is operable to adjust a predetermined lower rate to an elevated adjusted rate based on R-R intervals measured during a ventricular response detection time window associated with mode switching; a pacing controller that is operable to limit an elevated adjusted lower rate based on a programmed maximum pacing rate; a pacing controller that is operable to control the pacing rate based on an activity sensor indicated pacing rate; a pacing controller that is operable to decelerate an elevated adjusted lower rate towards a predetermined basic pacing rate (e.g., a programmed rate) that is as fast or faster than the predetermined lower rate; a pacing controller that is operable to readjust an elevated adjusted lower rate during a deceleration window based on intrinsic ventricular activity and to control deceleration of the readjusted elevated lower rate during a reinitiated deceleration period; and a pacing controller that is operable to continue deceleration to a predetermined basic pacing rate if no intrinsic ventricular activity is sensed during a deceleration window and thereafter continue to use the predetermined basic pacing rate until either intrinsic ventricular activity is sensed and a new readjusted elevated lower rate is reset for deceleration during another reinitiated deceleration period or the mode of operation is switched back.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

The present invention will be further described with reference to the drawings, wherein.

DETAILED DESCRIPTION OF THE EMBODIMENTS

Figure 1:
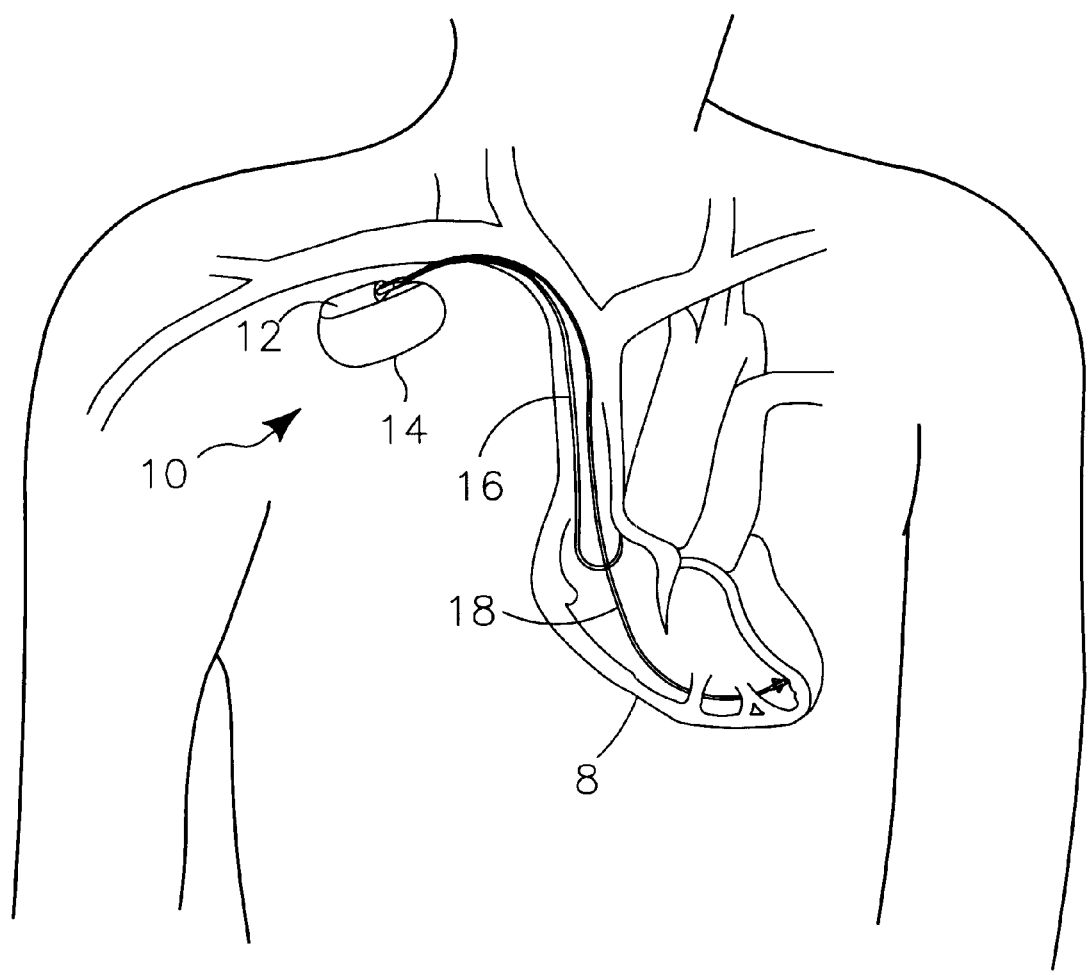
FIG. 1 is an implantable medical device (IMD) in accordance with one embodiment of the invention, wherein the IMD is implanted within a body of a patient.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18, sense electrical signals attendant to the depolarization and re-polarization of the heart 8, and further provide pacing pulses for causing depolarization of cardiac tissue in the vicinity of the distal ends thereof. Leads 16 and 18 may have, for example, unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson.

Figure 2:
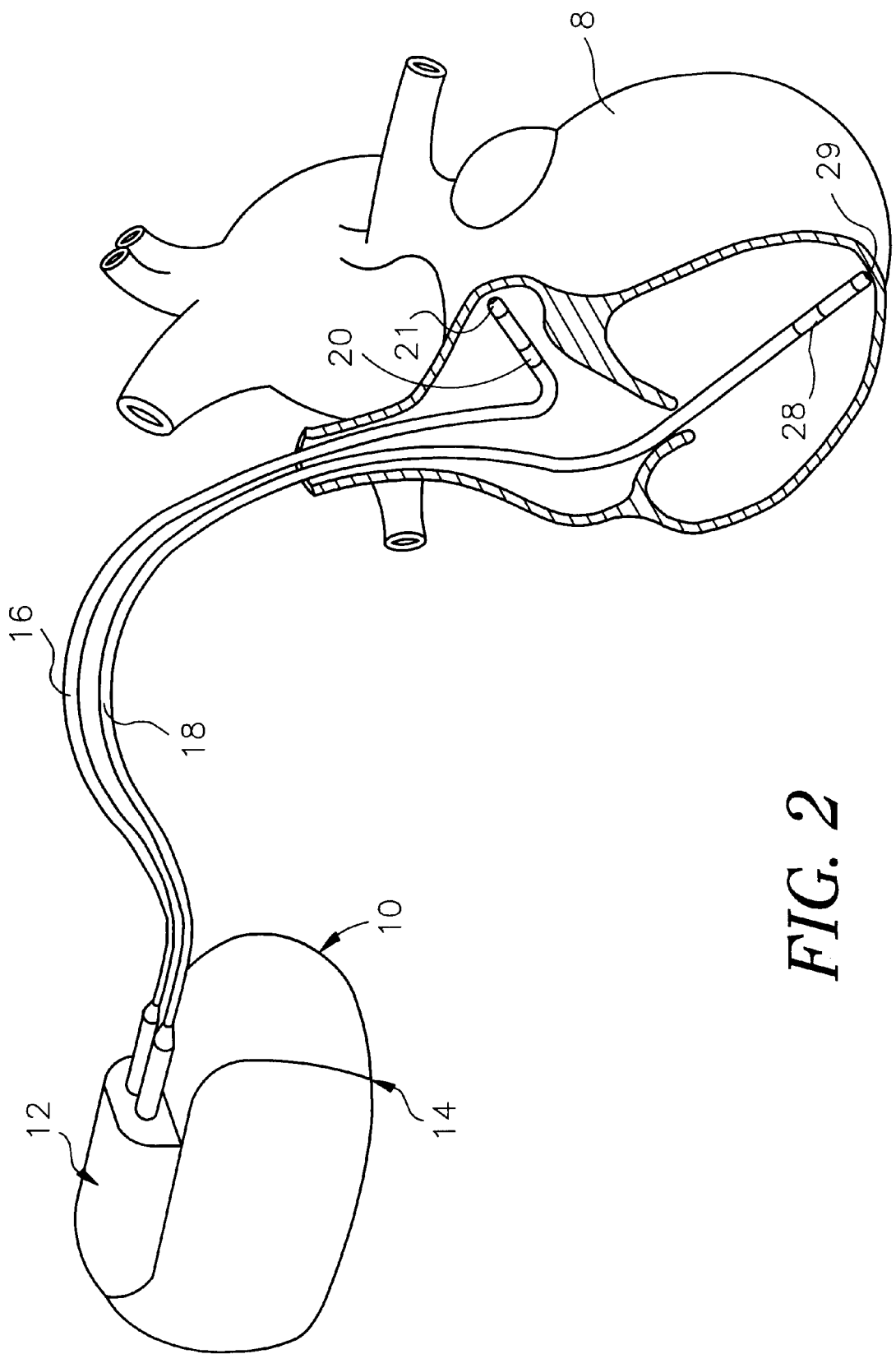
FIG. 2 is an enlarged view of the IMD of FIG. 1 diagrammatically illustrating coupling with the patient's heart in accordance with one embodiment of the invention.

FIG. 2 shows connector module 12 and hermetically sealed enclosure 14 of IMD 10 located near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
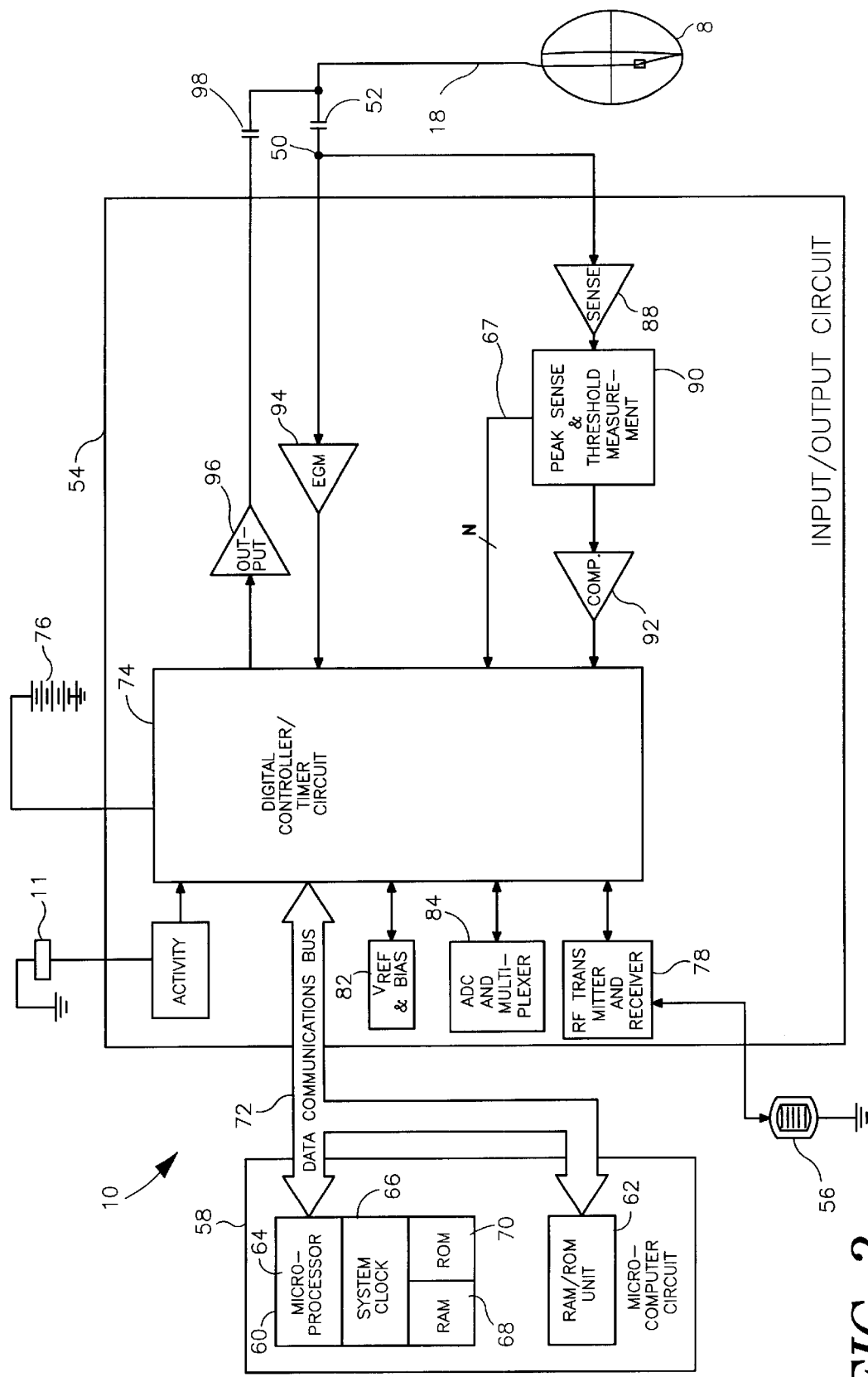
FIG. 3 is a functional block diagram of an IMD in accordance with one embodiment of the present invention.

FIG. 3 is a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,354,319 to Wyborny et al. The programming methodology disclosed in Wyborny et al.'s '319 patent is identified herein for illustrative purposes only. Any of a number of suitable programming and telemetry methodologies known in the art may be employed so long as the desired information is transmitted to and from IMD 10.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,556,063 issued to Thompson et al., or to that disclosed in the above-referenced '319 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

$V_{REF}$ and Bias circuit 82 (see FIG. 3) most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows, such as those described herein, for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al. Output pulse generator 96 provides pacing stimuli to patient's heart 8 through coupling capacitor 98, for example, in response to a pacing trigger signal provided by digital controller/timer circuit 74 each time the escape interval times out, in response to an externally transmitted pacing command or in response to other stored commands as is well known in the pacing art and as is described herein. By way of example, output amplifier 96 may correspond generally to an output amplifier disclosed in U.S. Pat. No. 4,476,868 to Thompson.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some embodiments of the present invention, IMD 10 may operate in various non-rate-responsive modes, including, but not limited to, DDD, DDI, WI, VOO and WT modes. In other embodiments of the present invention, IMD 10 may operate in various rate-responsive modes, including, but not limited to, DDDR, DDIR, WIR, VOOR and WTR modes. Some embodiments of the present invention are capable of operating in both non-rate-responsive and rate-responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to dual-sensor pacemakers, and is not limited to IMD's comprising activity or pressure sensors only. Further, the present invention is not limited in scope to dual-chamber pacemakers, dual-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of dual-, triple- or quadruple-chamber pacemakers or other types of IMD's. See, for example, U.S. Pat. No. 5,800,465 to Thompson et al. In one preferred embodiment, the present invention is particularly directed at pacing apparatus that provide bi-ventricular pacing therapy.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker, Jr. et al.

Figure 4:
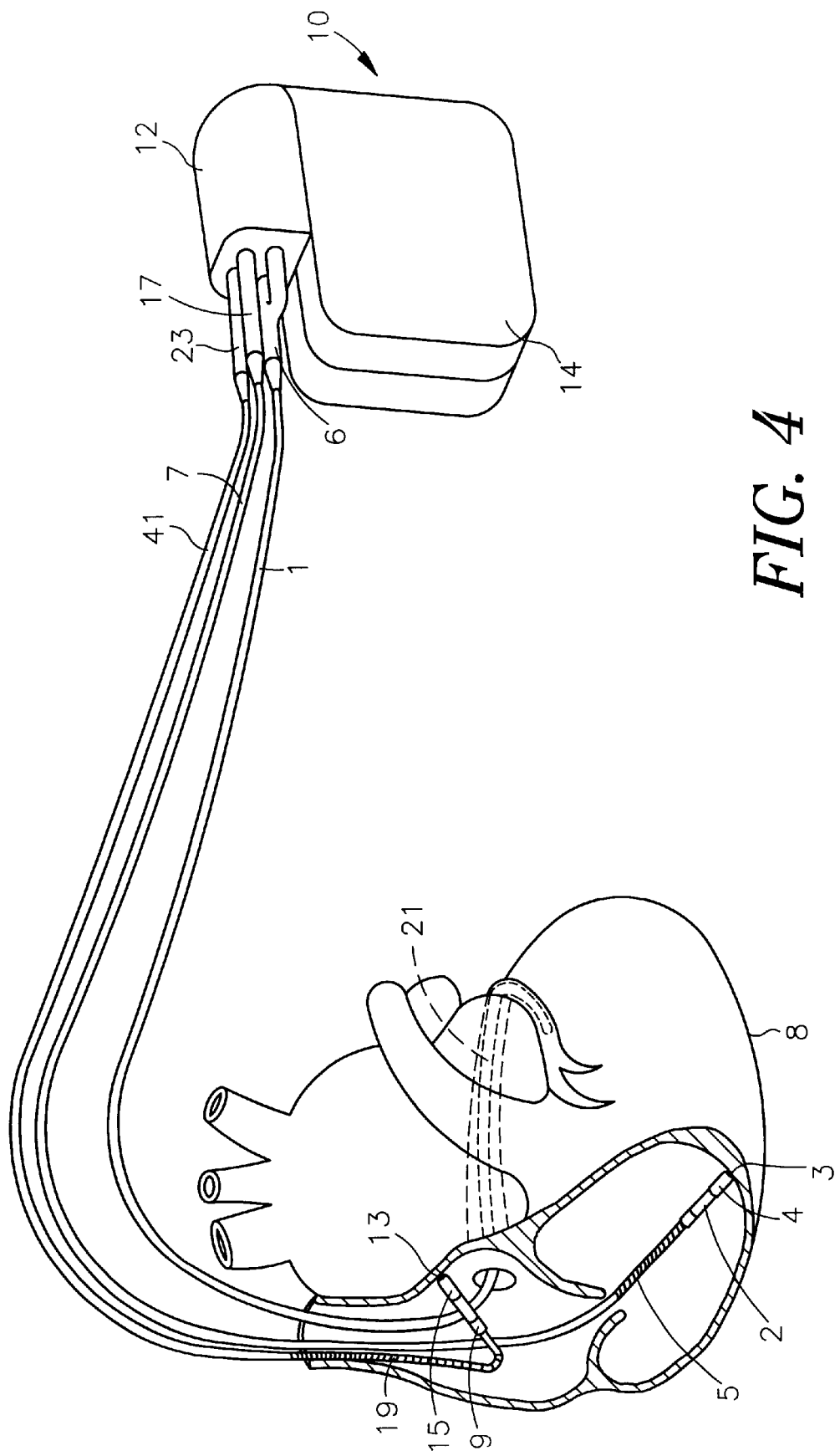
FIG. 4 is an IMD in accordance with another embodiment of the invention, wherein the IMD is an implantable pacemaker-cardioverter-defibrillator (PCD)
Figure 5:
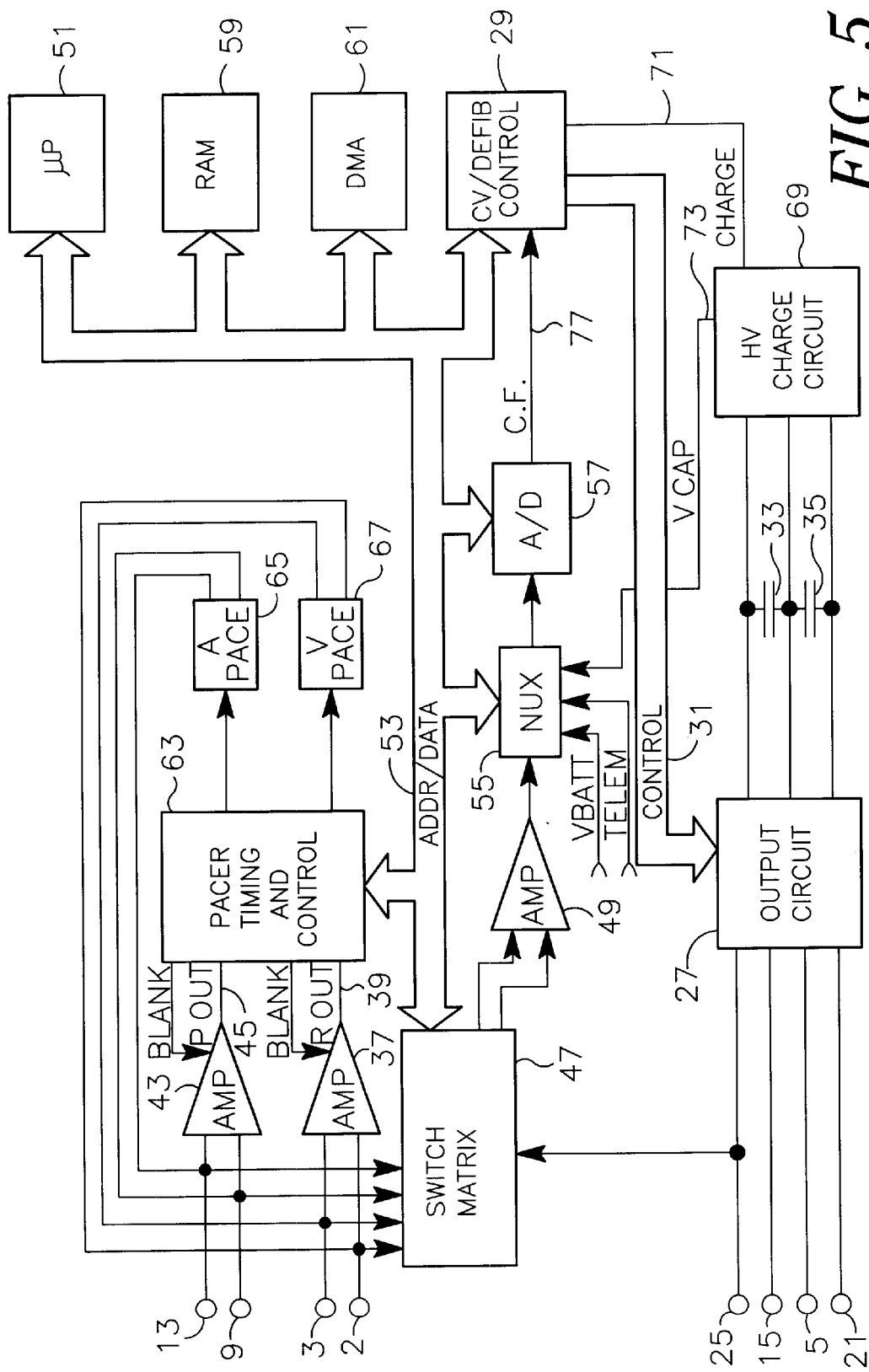
FIG. 5 is a functional block diagram of the IMD of FIG. 4.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

The implantable PCD is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al.

FIG. 5 is a functional schematic diagram of one embodiment of an implantable PCD of the present invention. This diagram should be taken as exemplary of the type of device in which various embodiments of the present invention may be embodied, and not as limiting, as it is believed that the invention may be practiced in a wide variety of device implementations which provided pacing therapies.

The PCD is provided with an electrode system. If the electrode configuration of FIG. 4 is employed, the electrode configuration correspondence may be as follows. Electrode 25 in FIG. 5 includes the uninsulated portion of the housing of the PCD. Electrodes 25, 15, 21 and 5 are coupled to high voltage output circuit 27, which includes high voltage switches controlled by CVldefib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, to Keimel et al.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selection may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known in the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, MI, DDI and other modes of single and dual chamber pacing well known to the art. Circuitry 63 also preferably controls escape intervals associated with anti-tachyarrhythmia pacing in both the atrium and the ventricle.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann et al., U.S. Pat. No. 4,880,005 issued to Pless et al. and U.S. Pat. No. 4,830,006 issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170. Atrial fibrillation detection methodologies are disclosed in Published PCT application Ser. No. US92/02829, Publication No. WO92/18198, by Adams et al., and in the article "Automatic Tachycardia Recognition", by Arzbaecher et al., published in PACE, May–June, 1984, pp. 541–547.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al. and U.S. Pat. No. 4,587,970, issued to Holley et al., may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and, in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al. However, any known cardioversion or defibrillation pulse control circuitry is believed to be usable in conjunction with various embodiments of the present invention. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. Examples of output circuitry for delivery of biphasic pulse regimens to multiple electrode systems may be found in U.S. Pat. No. 4,953,551 to Mehra et al. and in U.S. Pat. No. 4,727,877 to Kallock.

An example of circuitry which may be used to control delivery of monophasic pulses is disclosed in U.S. Pat. No. 5,163,427 to Keimel. Output control circuitry similar to that disclosed in the above-cited patent issued to Mehra et al. or U.S. Pat. No. 4,800,883 to Winstrom, may also be used in conjunction with various embodiments of the present invention to deliver biphasic pulses.

Figure 6:
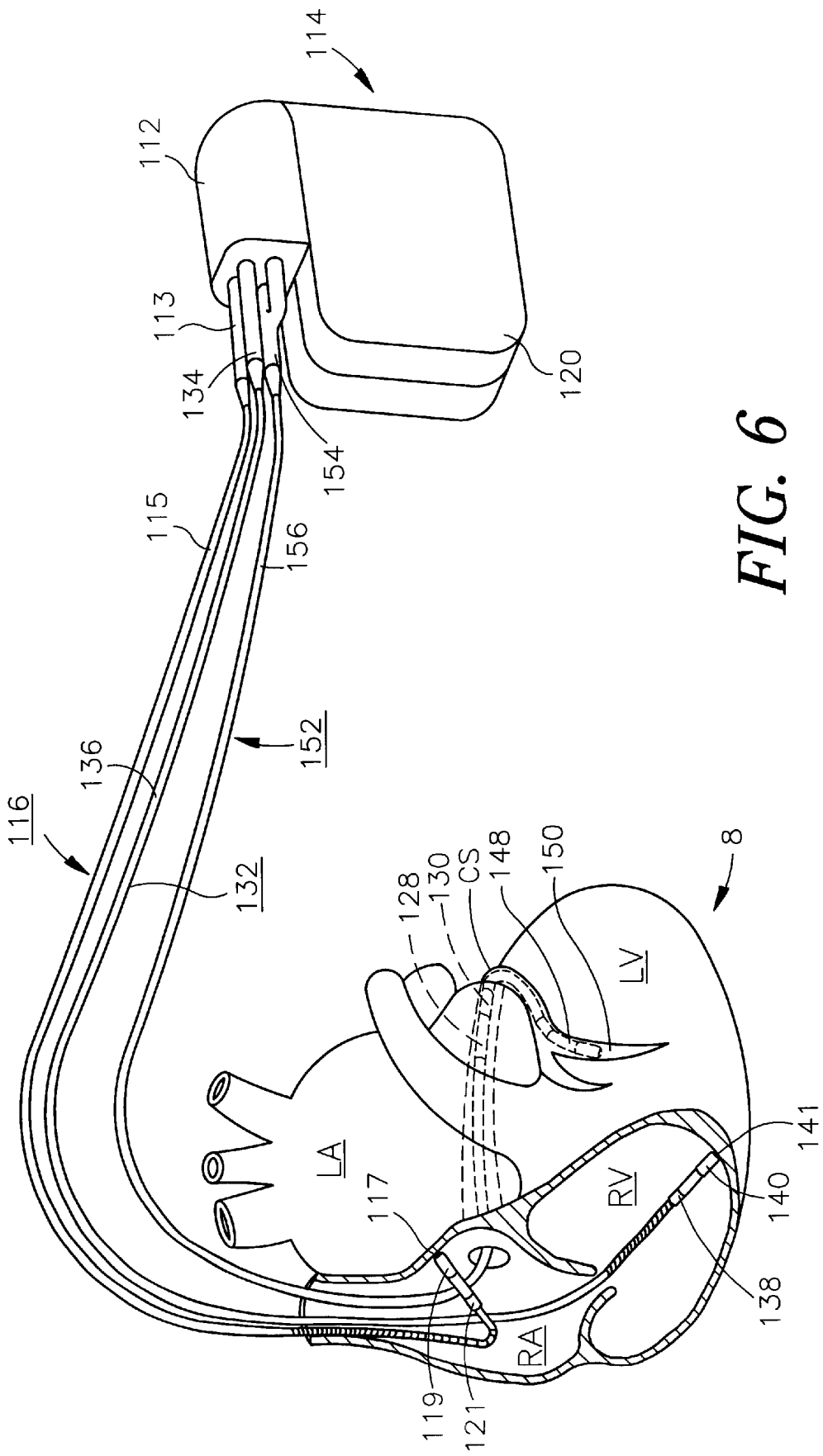
FIG. 6 is a diagram depicting a three or four channel, biatrial and/or bi-ventricular, pacing system according to one embodiment of the present invention.

FIG. 6 is a schematic representation of an implantable medical device (IMD) 114 including an implantable four-channel cardiac pacemaker such as that described in U.S. Pat. No. 6,070,101 to Struble et al. entitled "Multiple Channel, Sequential, Cardiac Pacing Systems," issued May 30, 2000. For example, such a pacemaker may provide bi-ventricular pacing therapy. The inline connector 113 of a right atrial lead 116 is fitted into a bipolar bore of IMD connector block 112 and is coupled to a pair of electrically insulated conductors within lead body 115 that are connected with distal tip right atrial pace-sense electrode 119 and proximal ring right atrial pace-sense electrode 121. The distal end of the right atrial lead 116 is attached to the right atrial wall by a conventional attachment mechanism 117. Bipolar endocardial right ventricle lead 132 is passed through the vein into the right atrial chamber of the heart 8 and into the right ventricle where its distal ring and tip right ventricular pace-sense electrodes 138 and 140 are fixed in place in the apex by a conventional and distal attachment mechanism 141. The right ventricular lead 132 is formed with an inline connector 134 fitting into a bipolar bore of IMD connector block 112 that is coupled to a pair of electrically insulated conductors within lead body 136 and then connected with distal tip right ventricular pace-sense electrode 140 and proximal ring right ventricular pace-sense electrode 138.

In this particular illustrative embodiment, although other types of leads may be used, a quadripolar, endocardial left ventricular coronary sinus (CS) lead 152 is passed through a vein into the right atrial chamber of the heart 8, into the CS, and then inferiorly in the great vein to extend to a distal pair of left ventricular CS pace-sense electrodes 148 and 150 alongside the left ventricular chamber and leave a proximal pair of left atrial CS pace-sense electrodes 128 and 130 adjacent the left atrial chamber. The left ventricular CS lead 152 is formed with a four-conductor lead body 156 coupled at the proximal end to a bifurcated inline connector 154 fitting into a pair of bipolar bores of IMD connector block 112. The four electrically insulated lead conductors in left ventricular CS lead body 156 are separately connected with one of the distal pair of left ventricular CS pace-sense electrodes 148 and 150 and the proximal pair of left atrial CS pace-sense electrodes 128 and 130.

The IMD 114 may comprise, for example, similar circuitry and connections as shown in FIG. 3 for each of the multiple leads to establish the multiple pacing/sensing channels provided for each respective pair of pace-sense electrodes associated with each chamber of the heart as shown in FIG. 6. For the sake of convenience, such circuitry is not described further. For example, channel circuitry for pacing/sensing the left atrial chamber is associated with pace-sense electrodes 28 and 30 adjacent the left atrium. One skilled in the art will recognize that each sensing/pacing channel may include a sense amplifier and pace output pulse generator coupled through the respective pacing/sensing lead. Although the pacing system shown in FIG. 6, shall not be described in detail for simplicity purposes, it will be recognized that multiple chambers may be paced/sensed via respective channels for such chambers. As such, for example, bi-atrial and/or bi-ventricular pacing may be performed as would be readily apparent to one skilled in the art.

With various embodiments of IMDs described above, it will become apparent from the description below that the present invention may be applied to any dual chamber pacing apparatus. For example, the present invention may be applied to a three-chamber atrial-bi-ventricular pacer, a dual chamber defibrillator, etc. Some devices that may be modified to include the techniques according to the present invention may include, for example, the InSync, InSync-ICD, or In Sync III three chamber atrial-biventricular pacers; all VDD(R)/DDD(R) pacemakers including dual chamber right atrial/left ventricular pacers; Jewel DR DDD(R)-ICD; dual chamber (right atrial/left ventricular) defibrillators, and three chamber DDD(R)-ICD pacing devices available from Medtronic Inc.

More particularly, the present invention may be applied to any implantable medical device capable of employing a mode switching operation. As used herein, mode switching is generally referred to as the switching from a first pacing mode that paces at least one ventricle based on sensed atrial activity, to a second pacing mode that paces the at least one ventricle based on sensed ventricular activity at a predetermined lower rate with such pacing inhibited based on intrinsic ventricular activity. Mode switching from the first pacing mode to the second pacing mode occurs, when atrial activity is detected above a predetermined/programmed mode switching rate. For example, mode switching is generally a standard feature in many dual chamber pacemakers. Generally, such mode switching provides for changing the operating mode of pacing therapy during periods of accelerated atrial arrhythmias such as SVT, PAF, and AF. For example, upon detection of periods of accelerated atrial arrhythmias, mode switching may change dual chamber pacing modes from DDD to DDI, DDDR to DDIR, VDD to VVI, or VDDR to VVIR.

During episodes of conventional mode switching due to accelerated atrial arrhythmia, generally the dual chamber pacemaker reverts to a lower rate (LR) pacing frequency in a standard DDI or VVI functionality (or if a rate responsive mode such as standard DDIR or VVIR is used, then the pacemaker reverts to either the lower rate (LR) or a rate response sensor indicated (RRSI) rate). As previously described herein, during such mode switching periods, an insufficient pacing rate and cardiac output may result. Further, in the case of bi-ventricular pacing for heart failure-type patients, continuous pacing therapy may be lost.

Figure 7:
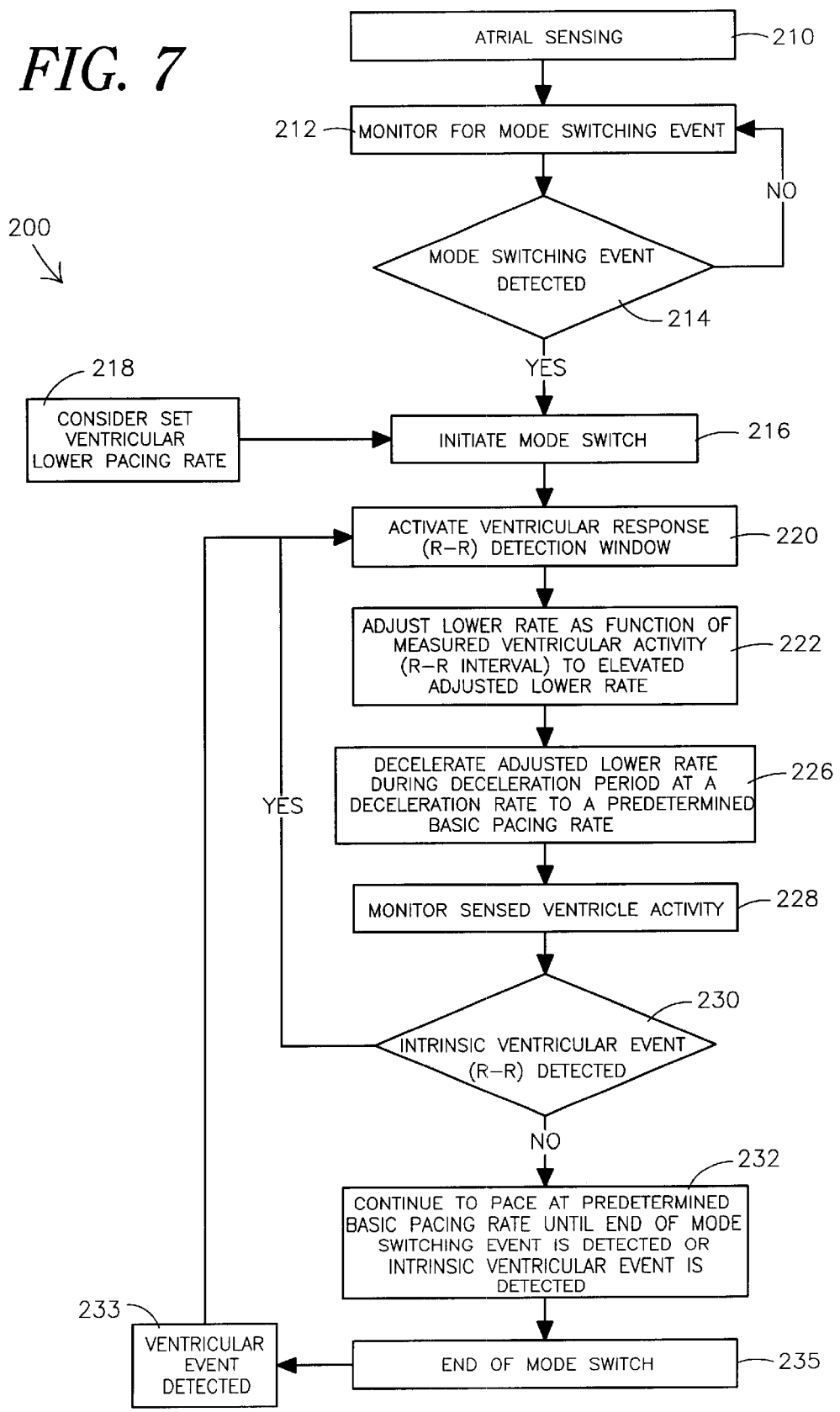
FIG. 7 is a flow diagram illustrating accelerated ventricular lower rate pacing according to the present invention.

FIG. 7 generally shows a flow diagram for providing accelerated LR pacing during episodes of mode switching to provide enhanced operation during such periods and alleviating or reducing the potential undesirable effects of mode switching. Accordingly, attention is directed to FIGS. 7–12.

Various embodiments of accelerated ventricular LR pacing according to the present invention shall be described with reference to such figures. The circuitry described previously herein, e.g., controller/timer circuit 74 of FIG. 3, includes programmable digital counters which control the basic timing intervals associated with various modes of pacing, e.g., DDD, DDI, VVI, VDD, as well as other modes of dual chamber pacing known in the art. Such circuitry controls escape intervals associated with anti-tachyarrhythmia pacing therapies employed as described herein and others known in the art. For example, intervals defined by pacing circuitry, e.g., input/output circuitry 54 of FIG. 3, include atrial and ventricular pacing escape intervals, the refractory periods during which sensed P-waves and R-waves are ineffective to restart timing of escape intervals, and the pulse widths of the pacing pulses. The durations of these intervals are determined by processing circuitry, e.g., microcomputer circuitry 58 of FIG. 3, in response to stored data in memory and are communicated to the pacing circuitry, e.g., digital controller/timer circuitry 74 of FIG. 3.

The duration of intervals defined by the escape interval timers are determined by processing circuitry. The value of the count present in escape interval counters when reset by sensed R-waves and P-waves may be used to measure the durations of R-R intervals, P-P intervals, P-R intervals, and R-P intervals, which measurements are stored in memory and can be used in conjunction with the present invention for a variety of functions, including to diagnose the occurrence of accelerated atrial arrhythmias.

Processor circuitry, e.g., microcomputer circuitry 58 as shown in FIG. 3, includes associated memory that may be configured for holding a series of measured intervals. Such measured intervals may be analyzed to determine whether a patient's heart is presently exhibiting atrial or ventricular tachyarrhythmia or to determine the fastest R-R interval during a sample period as described further below.

As shown in FIG. 7, the accelerated LR pacing method 200 includes the provision of atrial sensing (block 210) which is monitored for a mode switching event (block 212). More particularly, and preferably according to the present invention, such a mode switching event includes the detection of periods of accelerated atrial arrhythmia such as SVT, PAF, AF, etc.

The accelerated atrial arrhythmia detection method may include the use of any prior art tachyarrhythmia detection algorithms. Various atrial arrhythmia detection methods are available in implantable medical devices, such as those available from Medtronic. For example, many devices such as the InSync, InSync-ICD, or InSync III three chamber atrial-biventricular pacers; Jewel DR DDD(R)-ICD; and other pacing devices available from Medtronic Inc. provide various algorithms for detecting such accelerated atrial arrhythmias. However, any suitable arrhythmia detection methodologies known in the art may be employed.

As used herein, a mode switching event is defined as a period of accelerated atrial arrhythmia. Preferably, the detection of such a mode switching event leads to the switching of pacing modes in the pacing apparatus. Preferably, the pacing modes are switched from a first mode wherein at least one ventricle is paced based on sensed atrial activity, e.g., DDD, VDD, etc., to a second mode that paces the at least one ventricle based on sensed ventricular activity at the programmed LR with such pacing inhibited based on intrinsic ventricular activity, e.g., DDI, VVI, etc.

As shown in block 214, if no mode switching event is detected, then further monitoring is performed (block 212). However, according to the present invention, if a mode switching event is detected, then the mode switch is initiated (block 216). For example, if the dual chamber pacemaker was operating in DDD mode, then a DDI mode would be initiated. Likewise, if the pacemaker was operating in DDDR mode, then the mode may be switched to DDIR mode. If the pacemaker is operating in VDD mode, then the mode is switched to VVI, and, likewise, if the mode is operating in VDDR mode, then the mode may be switched to VVIR.

In other words, for example, with respect to the switching of the pacing mode from DDD to DDI upon the detection of a mode switching event, i.e., a period of accelerated atrial arrhythmia, pacing is no longer provided based on sensed atrial activity but rather ventricular pacing is paced upon sensed ventricular activity with pacing inhibited based on intrinsic ventricular events. In other words, a pacer in DDD mode may pace the ventricle in response to electrical activity sensed in the atrium. However, in DDI mode (which is virtually equivalent to VVI mode), the pacer paces and senses in the ventricle, but its pacing is inhibited by spontaneous electrical activation of the ventricle (i.e., intrinsic ventricular activity or events, or, in other words, the ventricle paces itself naturally).

Generally, a programmed ventricular LR is considered (block 218) for use in determining rates used in the second pacing mode upon initiation of a mode switch (block 216). At least in one embodiment, the LR (block 218) is programmed below that of the intrinsic rate of the patient's sinus rhythm, e.g., LR=60 ppm when SR=70 bpm. This programmed LR is restricted from being set too fast because if the LR is set too fast, it may compete with intrinsic activity of the heart. Preferably, it is desirable that the intrinsic activity control.

Therefore, as shown in FIG. 7, upon initiation of mode switching (block 216), the ventricular LR is used. For example, if no intrinsic ventricular activity is sensed in the ventricular chamber, then the ventricle is paced at the LR.

When sensed ventricular events are detected, then pacing is inhibited and the intrinsic ventricular activity controls.

Due to the problems previously described herein related to the use of the LR (block 218) in the second pacing mode, e.g., insufficient pacing rate and reduced cardiac output, the present invention provides accelerated LR pacing by activating a ventricular response (R-R) detection window (block 220) at least initially upon mode switching and adjusting the LR (block 218) at least initially to an elevated adjusted LR based on measurements taken during this window. The detection window may be a programmable window of sampling in the range of, preferably, about 5 seconds to 10 seconds. As used herein, the term "at least initially" refers to a time frame that does not necessarily mean that the window or the adjustment of the LR to the elevated adjusted LR is initiated or performed at the same time as the mode is switched but rather is initiated or performed at least a short time thereafter (e.g., preferably within 5 seconds to 10 seconds). For example, the programmed lower rate is not adjusted until after sampling is performed during the detection window which may be, for example, 5–10 seconds. As such, although the LR is "at least initially" adjusted to the elevated adjusted LR, this adjustment does not generally occur until after the detection window.

Following activation of the window (block 220), the programmed LR is then adjusted as a function of measured ventricular activity within the window to an elevated adjusted LR (block 222). The programmed LR is adjusted to an elevated adjusted LR such that pacing of the at least one ventricle is not inhibited based on intrinsic ventricular activity. In other words, preferably, the elevated adjusted LR is at a rate faster than the occurrence of intrinsic ventricular activity such that the intrinsic ventricular activity does not inhibit the pacemaker from pacing of the ventricle. In other words, as opposed to intrinsic ventricular activity controlling heart activity, the pacemaker takes control and at least one ventricle is paced at the elevated adjusted LR.

Figure 8:
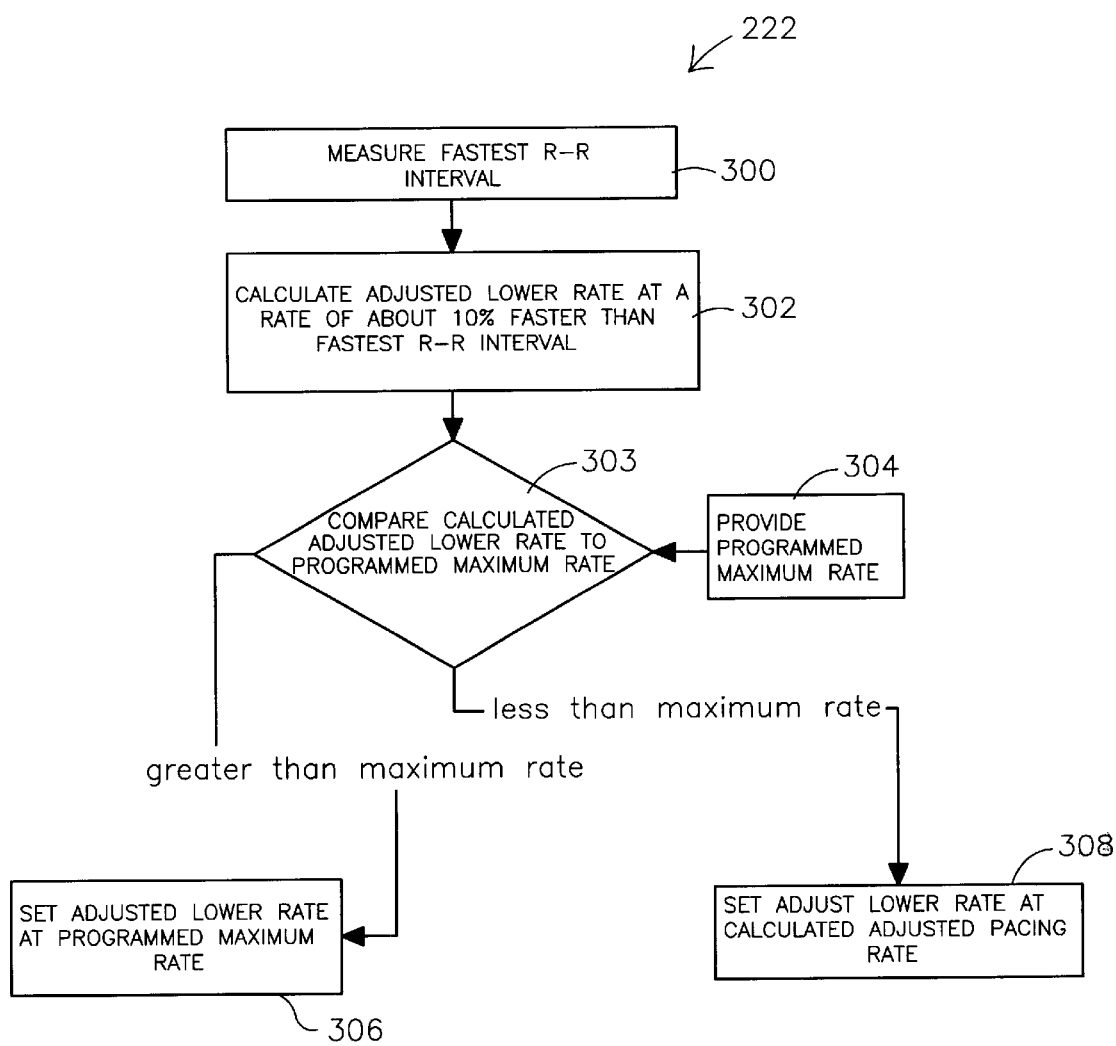
FIG. 8 is a flow diagram illustrating one illustrative embodiment of performing the adjustment of the lower rate as shown in FIG. 7 according to the present invention.

FIG. 8 generally shows one illustrative embodiment of a method 222 for adjusting the programmed LR as a function of measured ventricular activity during the ventricular response detection window. As shown therein, during the ventricular response detection window (e.g., a 5 second to 10 second sampling window), R-R intervals are measured and the elevated adjusted LR is determined based thereon. For example, the fastest R-R interval may be measured (block 300) for use in determining the initial elevated adjusted LR to deliver ventricular therapy. Upon measurement of the fastest R-R interval (block 300), the elevated adjusted LR is calculated (block 302).

In one exemplary embodiment, as shown in FIG. 8, the elevated adjusted LR may be determined by calculating the rate at about 10% faster than the fastest R-R interval. This ensures that continuous pre-excitation ventricular therapy is provided. For example, if the fastest R-R interval is 600 milliseconds (or 100 bpm), then the elevated adjusted LR may be 110 ppm (i.e., 100+10% thereof). One skilled in the art will recognize that the elevated adjusted LR may be calculated using various other methods or any other generally suitable percentage (for example, 9% faster than the fastest R-R interval), as long as the resulting elevated adjusted LR provides ventricular pacing that is not inhibited by intrinsic ventricular activity.

Further, for patient safety, a programmed maximum rate is also provided (block 304). This maximum rate for the elevated adjusted LR is preferably provided by a physician to protect patients in whom faster ventricular pacing is undesirable (e.g., ischaemic heart disease patients). For example, this maximum rate may be in the range of about 120 ppm to about 160 ppm depending upon the patient.

As shown in FIG. 8, upon calculation of the elevated adjusted LR (block 302), the calculated elevated adjusted LR is compared to the programmed maximum rate (block 303) to determine whether the elevated adjusted LR must be limited by the programmed maximum rate (block 304). As shown therein, if the elevated adjusted LR is greater than the programmed maximum rate, then the elevated adjusted LR is set at the programmed maximum rate (block 306). Otherwise, if the calculated elevated adjusted LR is less than the maximum programmed rate, then the calculated elevated adjusted LR is used (block 308). For example, if the maximum rate is programmed for a patient at 130 ppm and the calculated elevated adjusted LR is 140 ppm, then the calculated LR is limited by the programmed maximum rate of 130 ppm.

Further, with reference to FIG. 7, upon adjustment of the LR to the elevated adjusted LR (block 222) (e.g., following mode switching due to detection of a period of accelerated atrial arrhythmia), a deceleration period is provided during which the elevated adjusted LR is decelerated to a predetermined basic pacing rate (e.g., a programmed pacing rate) at a particular deceleration rate. By overdrive pacing using the initial elevated adjusted LR that ensures ventricular pacing therapy and thereafter decelerating the elevated adjusted LR to a predetermined basic pacing rate that is also preferably accelerated relative to the programmed LR (block 218), desirable cardiac output can be achieved.

The predetermined basic pacing rate is preferably as fast or faster than the programmed LR (block 218). Further, preferably, the programmed basic pacing rate is an elevated compensatory rate that guarantees sufficient cardiac output. More preferably, this predetermined or programmed basic pacing rate is programmed at the LR as considered in block 218 plus 20 ppm, e.g., 80 ppm. Preferably, the deceleration period is about 5 seconds to about 10 seconds and the elevated adjusted LR is gradually decelerated at a rate of about 5% to about 10% per cycle during the deceleration period.

Also during the deceleration period, ventricular response or ventricular activity is monitored (block 228). If an intrinsic ventricular event (R-R) is detected (block 230), then action must be taken for continuing to ensure ventricular pacing therapy. In other words, if intrinsic ventricular events are detected, then the decelerating elevated adjusted LR is not fast enough to control pacing of the heart. As such, upon detection of such intrinsic ventricular events (block 230), a ventricular response detection window is again re-activated or re-initiated (block 220) and the LR is once again adjusted to a readjusted elevated LR based upon measured activity in the detection window (block 222), e.g., adjusted based on the fastest R-R interval. Thereafter, the readjusted elevated LR is then again decelerated (block 226) during a reinitiated deceleration window, such as in the same manner as described previously above.

If the elevated adjusted LR is decelerated to the predetermined basic pacing rate with no intrinsic ventricular event being detected (block 230), then pacing at the predetermined basic pacing rate will continue until the end of the mode switching event is detected (block 232). For example, until accelerated atrial arrhythmias are no longer being detected, the ventricular pacing therapy is continued at the predetermined basic pacing rate. However, if a ventricular event is detected after the deceleration period is over and while the pacing is being continued at the predetermined basic pacing rate (block 233), then once again the detection window is reactivated (block 220) and the rate is readjusted to a new readjusted elevated LR (block 222) based on information measured in the detection window.

Mode switching is a semi-permanent mode change driven by sensed heart activity events and/or sensor derived events occurring in a first relationship wherein the device dictates that it remain in the mode it is changed to until those or others can satisfy a second defined relationship. In other words, until the switching back of the pacing device from the second pacing mode to the first pacing mode (block 235), e.g., DDI back to DDD, ventricular pacing therapy is performed at the predetermined basic pacing rate. In the present invention, for the mode to switch back from the second mode to the first mode, detected periods of accelerated atrial arrhythmias must have terminated in the patient.

The accelerated LR pacing method 200 described above generally with reference to FIG. 7, and also more particularly in part with reference to FIG. 8, will be described in more detail with respect to a particular illustrative delivered pacing therapy method 240 shown in the timing diagram of FIG. 9. This pacing therapy timing diagram 240 is representative of a pacing device providing bi-ventricular stimulation therapy. One skilled in the art will recognize that although this illustrative timing diagram 240 is provided with focus on bi-ventricular pacing in a heart failure patient, the present invention can be applied to any dual chamber pacing system with mode switching so as to accelerate the mode switching LR (e.g., LR of block 218) during periods of accelerated atrial arrhythmias. Such accelerated LR pacing compensates for loss in cardiac output during mode switching episodes, and is particularly important for patients who lose the "atrial kick" at low levels of activity. It is at these low heart rates that atrial kick has the greatest impact on ventricular filling. As such, the accelerated LR pacing provided in accordance with the present invention attempts to compensate for the loss of atrial kick during episodes of atrial arrhythmias and/or episodes of mode switching by elevating the ventricular pacing rate.

Figure 9:
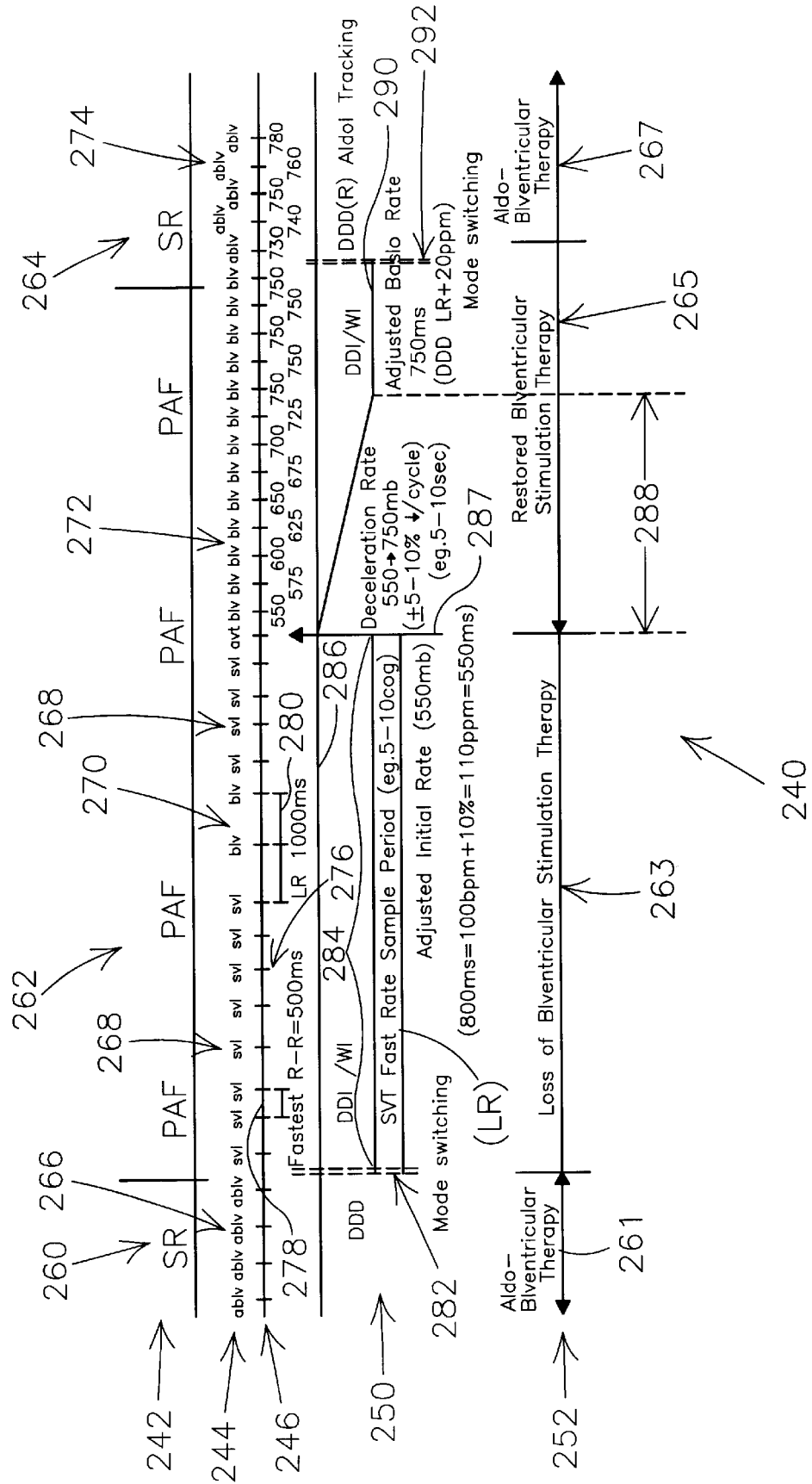
FIG. 9 is a timing diagram for use in illustrating the accelerated lower rate pacing shown in FIG. 7.

The timing diagram 240 shown in FIG. 9 includes a section 242 that is representative of the particular atrial sensed conditions, e.g., sinus rhythm, accelerated atrial arrhythmias such as SVT, PAF, etc.; a pacing section 244 that describes the type of pacing that is occurring during the timing diagram 240 such as atrial sensed bi-ventricular pacing (abiv), supraventricular tachyarrhythmia (svt), and bi-ventricular pacing (biv); a section 246 that is indicative of ventricular response or R-R intervals; an accelerated LR pacing section 250 that is illustrative of the adjustment of pacing rates according to the present invention; and a therapy identification section 252 that indicates the occurrence and loss of therapy during the timing diagram 240.

As shown in FIG. 9, during a first period of time 260, normal sinus rhythm is sensed. With the pacing apparatus operating in DDD/VDD pacing mode, atrial bi-ventricular therapy 261 is provided as shown by the atrial sensed bi-ventricular pacing 266 shown in section 244 along with a stable R-R interval pattern shown in section 246. Following this episode of sinus rhythm 260, accelerated atrial arrhythmia is detected in the form of PAF during a subsequent period 262. Upon detection of the accelerated atrial arrhythmia, i.e., PAF, mode switching 282 occurs and the first pacing mode (i.e., DDD/VDD) is switched to the second pacing mode (i.e., DDI/VVI). In this particular example, the programmed LR for the second mode of pacing (i.e., DDI/VVI) is set at 1,000 milliseconds or an LR=60 ppm.

Upon the detection of the accelerated atrial arrhythmia, a ventricular response detection window 284, e.g., a SVT fast rate sample period, is initiated. As shown in FIG. 9, the ventricular response detection window is about 5–10 seconds. During this ventricular response detection window 284, there is a loss of bi-ventricular stimulation therapy 263. In other words, supra-ventricular tachycardia as shown in section 244 inhibits bi-ventricular pacing, i.e., pacemaker stimulation. This is directly evident from the changing R-R intervals shown in section 246 which follow the accelerated atrial arrhythmia. During two particular cycles, bi-ventricular pacemaker stimulation or bi-ventricular pacing (biv) occurs at the programmed LR of 1,000 milliseconds. This pacemaker bi-ventricular stimulation during these two cycles 280 occurs due to the lack of ventricular activity or intrinsic ventricular activity being sensed.

As can be seen by the regions of time represented by reference numerals 268 representative of supraventricular tachycardia, during most of the ventricular response detection windows 284, cardiac output is substantially reduced. This would be the case throughout the second mode of pacing without use of the present invention. However, such reduced cardiac output only occurs within the ventricular response detection window 284 as this sampling period is used to determine an elevated adjusted LR to capture the heart and be used to pace it thereafter.

During the ventricular response detection window 284, the R-R intervals are measured, and the fastest R-R interval is determined. In FIG. 9, the fastest R-R interval is equal to 600 milliseconds, as shown by reference numeral 278. The elevated adjusted LR 286 is then determined based upon the measured fastest R-R interval 278. In other words, the elevated adjusted LR may be calculated as the fastest R-R interval plus 10%, which in FIG. 9 is equal to 100 beats per minute plus 10%, or, in other words, 110 ppm (i.e., a rate of about 550 milliseconds).

As such, at the end 287 of the ventricular response detection window 284, the programmed LR is adjusted to the elevated adjusted LR 286 equal to 110 ppm. Therefore, due to the elevated nature of the LR (i.e., a LR greater than the intrinsic ventricular R-R intervals) bi-ventricular stimulation therapy 265 is restored. This is further shown by bi-ventricular pacing (biv) 272 (see section 244) which in the initial portion thereof shows pacing at the elevated adjusted LR 286 of about 550 milliseconds. As such, this elevated adjusted LR 286 of 550 milliseconds ensures that continuous bi-ventricular pacing therapy is delivered by the pacemaker.

The elevated adjusted LR 286 is used initially at time period 287 and then is decelerated during deceleration period 288. As shown in the illustrative embodiment of FIG. 9, the deceleration period may be in the range of about 5–10 seconds. Further, the elevated adjusted LR 286 is decelerated at 5–10% per cycle. As shown therein, the deceleration continues from the elevated adjusted LR 286 of about 550 milliseconds to a predetermined (i.e., programmed) basic pacing rate 290 of 750 milliseconds.

As previously described herein, the predetermined basic pacing rate 290 is programmed by the physician to preferably an elevated compensatory rate that guarantees sufficient cardiac output. As shown in FIG. 9, the programmed basic pacing rate 290 is set at the LR rate (i.e., 1,000 milliseconds or 60 ppm) plus 20 ppm=80 ppm or a 750 millisecond basic pacing rate 290.

In the embodiment of FIG. 9, there were no intrinsic ventricular events sensed during the restored bi-ventricular stimulation therapy period 265, and therefore bi-ventricular stimulation (biv) 272 occurs at the decelerating rate and thereafter at the predetermined basic rate 290 for the remainder of this period 265. However, if an intrinsic ventricular event would have been detected, a ventricular response detection window 284 would have been reinitiated and a new readjusted LR set for deceleration during a reinitiated deceleration period 288. However, as no intrinsic ventricular event was detected, the elevated programmed basic pacing rate 290 is used for bi-ventricular stimulation therapy until sinus rhythm 264 is reestablished. As such, upon the reestablishment of sinus rhythm, accelerated atria arrhythmias are no longer being detected and the second pacing mode, i.e., DDI/VVI mode, is switched back to first pacing mode, i.e., DDD/VDD, and atrial sensed bi-ventricular pacing 274 is once again provided for performing atrial bi-ventricular therapy 267.

As previously described herein, the elevated adjusted LR 286 determined using the measurements of R-R intervals during the ventricular response detection window 284 may be limited by a programmed maximum rate. For example, if the elevated adjusted LR 286 would have been determined to be 135 ppm and a programmed maximum rate was 130 ppm, the elevated adjusted LR 286 would have been limited to the maximum rate of 130 ppm.

Figure 10:
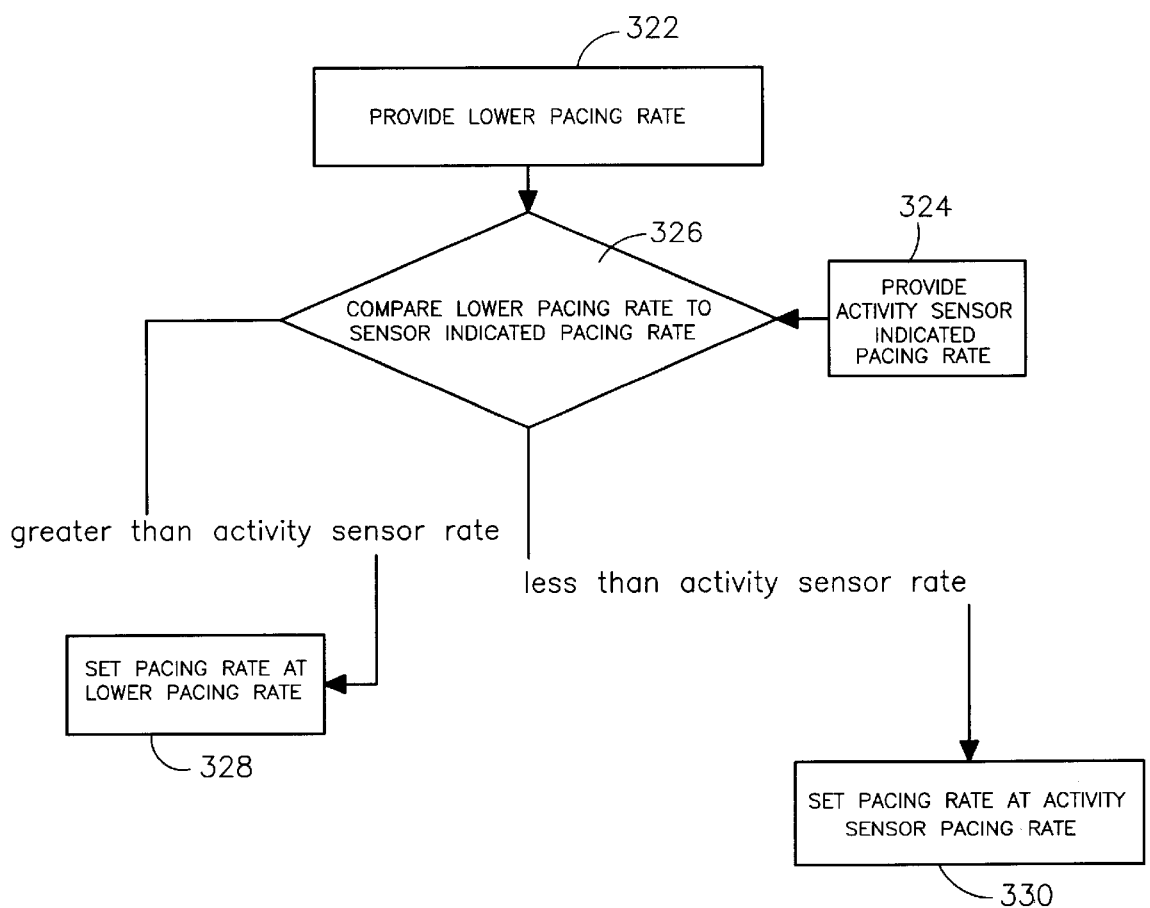
FIGS. 10–12 show flow diagrams illustrating the interaction of activity sensor indicated rates in conjunction with the accelerated lower rate pacing of FIG. 7.
Figure 11:
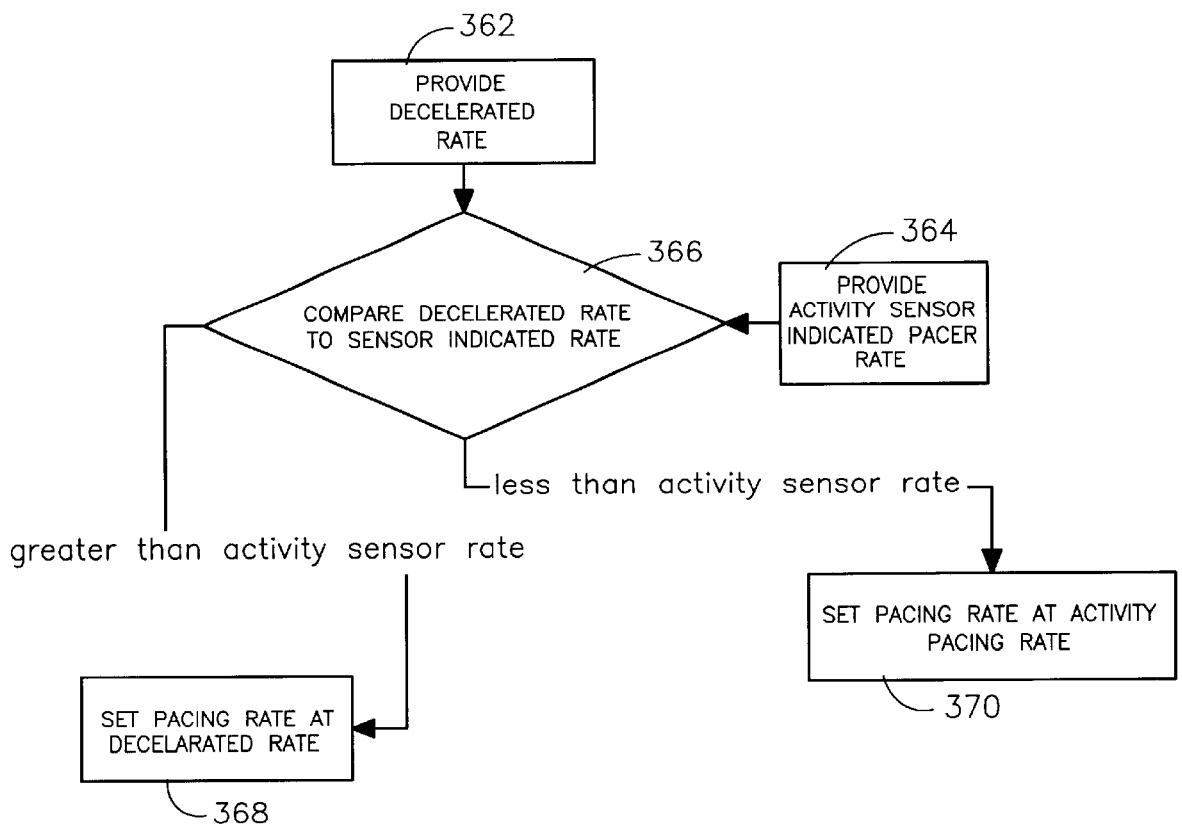
Figure 12:
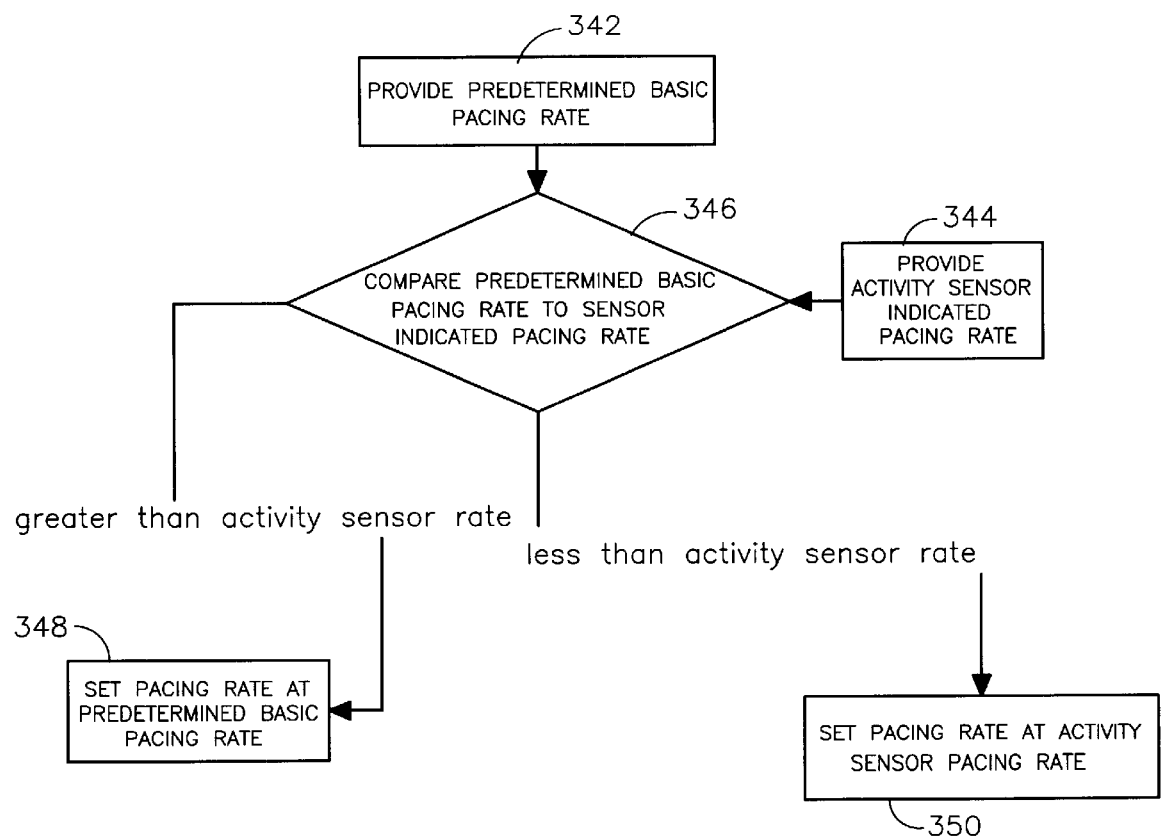

FIGS. 10–12 are provided to show the interaction of the present invention with pacing modes that also take into consideration, or are rate modulated by, the physical activity level of the patient. For example, pacing devices commonly use accelerometers to provide an indication of the patient's level of physical activity and which generally calculate a rate response sensor indicated (RRSI) rate based thereon. For example, such RRSI rates may be used in pacing apparatus operating in DDDR mode and switching to a DDIR mode upon the detection of accelerated atrial arrhythmias or, likewise, operating in a VDDR mode and switching to a VVIR mode upon detection of accelerated atrial arrhythmias, i.e., detection of a mode switching event.

Generally, if the RRSI rate is greater than any of the pacing rates determined according to the algorithms described with reference to FIGS. 7–9, then the RRSI rate will have priority to determine the pacing rate. This assumes that the activity sensor is optimized for the patient, and therefore, that the RRSI rate is more appropriate for the patient when the patient is undertaking such activity, e.g., exercise.

As shown in FIG. 10, the programmed LR is provided (block 322) and an RRSI rate or an activity sensor indicated pacing rate is also provided (block 324). During the ventricular response detection window, e.g., 284 of FIG. 9, the RRSI rate is compared to the programmed LR (block 326). If the programmed LR is greater than the RRSI rate, then the programmed LR is utilized (block 328). However, if the programmed LR is less than the RRSI rate, then the RRSI rate or the activity sensing indicated pacing rate is used (block 330). For example, in the illustrative embodiment shown in FIG. 9, if the LR is equal to 1,000 milliseconds and the RRSI rate provided per block 324 is equal to 750 milliseconds, then the RRSI rate would have priority to determine the pacing rate during the ventricular response detection window 284.

As shown in FIG. 11, an elevated adjusted LR or a decelerated rate is provided (block 362) and, again, an RRSI rate or activity sensor indicated pacing rate is provided (block 364). Such rates are compared (block 366) to determine which rate is the more appropriate rate to be used during the deceleration period. If the elevated adjusted LR or decelerated rate is greater than the RRSI rate, then the elevated adjusted LR or decelerated rate has priority (block 368), whereas if the elevated adjusted LR or decelerated rate is less than the RRSI rate, then the RRSI rate has priority (block 370). For example, as shown in FIG. 9, if at the time the decelerating rate is 625 milliseconds during the deceleration period 288 and the RRSI rate is indicated to be 600 milliseconds, the RRSI rate will have priority to determine the pacing rate.

Likewise, as shown in FIG. 12, the predetermined or programmed basic pacing rate is provided (block 342) along with the RRSI rate or activity sensor indicated pacing rate (block 344). Again, such rates are compared (block 346) to determine which rate has priority to determine the pacing rate. If the predetermined programmed basic pacing rate is greater than the RRSI rate, then it has priority (block 348). On the other hand, if the programmed basic pacing rate is less than the RRSI rate, then the RRSI rate has priority (block 350). For example, as shown in FIG. 9, the adjusted programmed basic rate 290 is programmed at about 750 milliseconds. If the RRSI rate is 600 milliseconds, then the RRSI rate of 600 milliseconds would have priority to determine the pacing rate during the restored bi-ventricular stimulation therapy 265.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative applications may utilize the accelerated LR pacing according to the present invention. Various modifications of the illustrative embodiments, as well as additional embodiments of the invention, will be apparent to persons skilled in the art upon reference to this description.

What is claimed is:

1. An implantable medical device method of pacing, the method comprising:

detecting a period of accelerated atrial arrhythmias;

switching from a first pacing mode to a second pacing mode upon detection of the period of accelerated atrial arrhythmias, wherein the first pacing mode paces at least one ventricle based on sensed atrial activity, and further wherein the second pacing mode paces the at least one ventricle based on sensed ventricular activity at a predetermined lower rate with such pacing inhibited based on intrinsic ventricular activity; and at least initially, upon switching from the first pacing mode to the second pacing mode, adjusting the lower rate to an elevated adjusted lower rate such that pacing of the at least one ventricle is not inhibited based on intrinsic ventricular activity.

2. The method of claim 1, wherein adjusting the lower rate to an elevated adjusted lower rate comprises adjusting the lower rate to an elevated adjusted lower rate based on R-R intervals measured during a ventricular response detection time window associated with switching from the first pacing mode to the second pacing mode.

3. The method of claim 2, wherein adjusting the lower rate to the elevated adjusted lower rate comprises:

measuring one or more R-R intervals during the ventricular response detection time window;

detecting at least the fastest R-R interval occurring during the ventricular response detection time window; and adjusting the lower rate to the elevated adjusted lower rate based on at least the fastest R-R interval measured during the ventricular response detection time window.

4. The method of claim 2, wherein adjusting the lower rate to the elevated adjusted lower rate comprises:
   determining the elevated adjusted lower rate based on R-R intervals measured during the ventricular response detection time window; and
   limiting the elevated adjusted lower rate based on a programmed maximum pacing rate.

5. The method of claim 2, wherein adjusting the lower rate to the elevated adjusted lower rate comprises:
   determining the elevated adjusted lower rate based on R-R intervals measured during the ventricular response detection time window;
   comparing the elevated adjusted lower rate to an activity sensor indicated pacing rate; and
   using either the elevated adjusted lower rate or the activity sensor indicated pacing rate based on the comparison.

6. The method of claim 1, wherein the method further comprises decelerating from the elevated adjusted lower rate towards a predetermined basic pacing rate that is as fast or faster than the predetermined lower rate.

7. The method of claim 6, wherein decelerating from the elevated adjusted lower rate towards the predetermined basic pacing rate comprises:
   decelerating from the elevated adjusted lower rate towards the predetermined basic pacing rate during a deceleration period;
   monitoring ventricular activity to detect any intrinsic ventricular events during the deceleration period; and
   readjusting the elevated adjusted lower rate upon detection of an intrinsic ventricular event during the deceleration period and decelerating the readjusted elevated lower rate during a reinitiated deceleration period.

8. The method of claim 6, wherein decelerating from the elevated adjusted lower rate towards the predetermined basic pacing rate further comprises continuing deceleration to the predetermined basic pacing rate if no intrinsic ventricular events are detected during the deceleration period and thereafter continuing to use the predetermined basic pacing rate until either an intrinsic ventricular event is detected and a readjusted elevated lower rate is reset for deceleration during another deceleration period or operation is switched from the second pacing mode back to the first pacing mode.

9. The method of claim 6, wherein decelerating from the elevated adjusted lower rate towards the predetermined basic pacing rate comprises:
   comparing the decelerating elevated adjusted lower rate to an activity sensor indicated pacing rate; and
   using either the decelerating elevated adjusted lower rate or the activity sensor indicated pacing rate based on the comparison.

10. The method of claim 1, wherein switching from the first pacing mode to the second pacing mode comprises switching from a DDD, DDDR, VDD, or VDDR pacing mode to a DDI, DDIR, VVI, or VVIR pacing mode, respectively.

11. The method of claim 1, wherein t he implantable medical device comprises a bi-ventricular pacing apparatus, a dual chamber pacing apparatus, and a pacemaker/cardioverter/defibrillator.

12. An implantable medical device method of pacing, the method comprising:
   switching from a DDD, DDDR, VDD, or VDDR first pacing mode to a DDI, DDIR, VVI, or VVIR second pacing mode, respectively, upon detection of a period of accelerated atrial arrhythmia, wherein the second pacing mode has an associated predetermined lower pacing rate;
   at least initially, upon switching from the first pacing mode to the second pacing mode, adjusting the predetermined lower pacing rate to an elevated adjusted lower rate; and
   decelerating from the elevated adjusted lower rate towards a programmed basic pacing rate during a deceleration period, wherein the programmed basic pacing rate is as fast or faster than the predetermined lower pacing rate.

13. The method of claim 12, wherein adjusting the predetermined lower pacing rate associated with the second pacing mode to the elevated adjusted lower rate comprises adjusting the predetermined lower pacing rate to an elevated adjusted lower rate based on R-R intervals measured during a ventricular response detection time window associated with switching from the first pacing mode to the second pacing mode.

14. The method of claim 13, wherein adjusting the predetermined lower pacing rate to the elevated adjusted lower rate comprises:
   measuring one or more R-R intervals during the ventricular response detection time window;
   detecting at least the fastest R-R interval occurring during the ventricular response detection time window; and
   adjusting the predetermined lower pacing rate to the elevated adjusted lower rate based on at least the fastest R-R interval measured during the ventricular response detection time window.

15. The method of claim 13, wherein adjusting the predetermined lower pacing rate to the elevated adjusted lower rate comprises:
   determining the elevated adjusted lower rate based on R-R intervals measured during the ventricular response detection time window; and
   limiting the elevated adjusted lower rate based on a programmed maximum pacing rate.

16. The method of claim 12, wherein switching from the DDD, DDDR, VDD, or VDDR first pacing mode to the DDI, DDIR, VVI, or VVIR second pacing mode, respectively, upon detection of a period of accelerated atrial arrhythmia comprises switching from a DDDR or VDDR first pacing mode to a DDIR or VVIR second pacing mode, respectively, upon detection of a period of accelerated atrial arrhythmia, and further wherein adjusting the predetermined lower pacing rate associated with the second pacing mode to an elevated adjusted lower rate comprises:
   determining the elevated adjusted lower rate based on R-R intervals measured during the ventricular response detection time window;
   comparing the elevated adjusted lower rate to an activity sensor indicated pacing rate; and
   using either the elevated adjusted lower rate or the activity sensor indicated pacing rate based on the comparison.

17. The method of claim 12, wherein decelerating from the elevated adjusted lower rate towards the programmed basic pacing rate comprises:
   monitoring to sense any intrinsic ventricular activity during the deceleration period; and
   readjusting the elevated adjusted lower rate upon detection of intrinsic ventricular activity during the deceleration period and decelerating the readjusted elevated lower rate during a reinitiated deceleration period.

18. The method of claim 12, wherein decelerating from the elevated adjusted lower rate towards the programmed basic pacing rate further comprises continuing deceleration to the programmed basic pacing rate if no intrinsic ventricular activity is detected during the deceleration period and thereafter continuing use of the programmed basic pacing rate until either intrinsic ventricular activity is detected and a new readjusted elevated lower rate is reset for deceleration during another deceleration period or operation is switched from the second pacing mode back to the first pacing mode.

19. The method of claim 12, wherein switching from the DDD, DDDR, VDD, or VDDR first pacing mode to the DDI, DDIR, VVI, or VVIR second pacing mode, respectively, upon detection of a period of accelerated atrial arrhythmia comprises switching from a DDDR or VDDR first pacing mode to a DDIR or VVIR second pacing mode, respectively, upon detection of a period of accelerated atrial arrhythmia, and further wherein decelerating from the elevated adjusted lower rate towards the programmed basic pacing rate comprises:

comparing the decelerating elevated adjusted lower rate to an activity sensor indicated pacing rate; and using either the decelerating elevated adjusted lower rate or the activity sensor indicated pacing rate based on the comparison.

20. The method of claim 12, wherein the implantable medical device comprises a bi-ventricular pacing apparatus, a dual chamber pacing apparatus, and a pacemaker/cardioverter/defibrillator.

21. An implantable medical device comprising:

pacing generator circuitry operable to generate pacing pulses at one or more pacing rates during at least first and second pacing modes, wherein the first pacing mode paces at least one ventricle based on sensed atrial activity, and further wherein the second pacing mode paces the at least one ventricle based on sensed ventricular activity at a predetermined lower rate with such pacing inhibited based on intrinsic ventricular activity;

sensing circuitry operable to sense atrial and ventricular activity; and a pacing controller operable to switch from the first pacing mode to the second pacing mode upon detecting a period of accelerated atrial arrhythmias based on information from the sensing circuitry, wherein the pacing controller is further operable to at least initially, upon switching from the first pacing mode to the second pacing mode, adjust the predetermined lower rate to an elevated adjusted lower rate such that pacing of the at least one ventricle is not inhibited based on detected intrinsic ventricular activity.

22. The device of claim 21, further wherein the pacing controller is operable to adjust the predetermined lower rate to the elevated adjusted lower rate based on R-R intervals measured during a ventricular response detection time window associated with switching from the first pacing mode to the second pacing mode.

23. The device of claim 22, further wherein the pacing controller is operable to:

measure one or more R-R intervals during the ventricular response detection time window based on information from the sensing circuitry;

determine at least the fastest R-R interval occurring during the ventricular response detection time window; and adjust the predetermined lower rate to the elevated adjusted lower rate based on at least the fastest R-R interval measured during the ventricular response detection time window.

24. The device of claim 22, further wherein the pacing controller is operable to:

determine the elevated adjusted lower rate based on R-R intervals measured during the ventricular response detection time window; and limit the elevated adjusted lower rate based on a programmed maximum pacing rate.

25. The device of claim 24, further wherein the pacing controller is operable to:

determine the elevated adjusted lower rate based on R-R intervals measured during the ventricular response detection time window;

compare the elevated adjusted basic pacing rate to an activity sensor indicated pacing rate; and control the pacing rate by using either the elevated adjusted lower rate or the activity sensor indicated pacing rate based on the comparison.

26. The device of claim 21, wherein the pacing controller is further operable to decelerate the elevated adjusted lower rate towards a predetermined basic pacing rate that is as fast or faster than the predetermined lower rate.

27. The device of claim 26, further wherein the pacing controller is operable to:

control deceleration from the elevated adjusted lower rate towards the predetermined basic pacing rate during a deceleration period; and readjust the elevated adjusted lower rate during the deceleration period based on intrinsic ventricular activity sensed by the sensing circuitry and control deceleration of the readjusted elevated lower rate during a reinitiated deceleration period.

28. The device of claim 26, wherein the pacing controller is further operable to continue deceleration to the predetermined basic pacing rate if no intrinsic ventricular activity is sensed during the deceleration window and thereafter continue to use the predetermined basic pacing rate until either intrinsic ventricular activity is sensed and a new readjusted elevated lower rate is reset for deceleration during another deceleration period or operation is switched from the second pacing mode back to the first pacing mode.

29. The device of claim 26, further wherein the pacing controller is operable to:

compare the decelerating elevated adjusted lower rate to an activity sensor indicated pacing rate; and use either the decelerating elevated adjusted lower rate or the activity sensor indicated pacing rate based on the comparison.

30. The device of claim 21, wherein the pacing controller is operable to switch from a DDD, DDDR, VDD, or VDDR first pacing mode to a DDI, DDIR, VVI, or VVIR second pacing mode, respectively.

31. The device of claim 21, wherein the implantable medical device comprises a bi-ventricular pacing apparatus, a dual chamber pacing apparatus, and a pacemaker/cardioverter/defibrillator.

32. An implantable medical device comprising:

pacing generator circuitry operable to generate pacing pulses at one or more pacing rates during at least first and second pacing modes, wherein the first pacing mode comprises a DDD, DDDR, VDD, or VDDR pacing mode and wherein the second pacing mode comprises a DDI, DDIR, VVI, or VVIR pacing mode, and further wherein the DDI, DDIR, VVI, or VVIR second pacing mode has an associated programmed lower pacing rate;

sensing circuitry operable to sense atrial and ventricular activity; and a pacing controller operable to switch from the DDD, DDDR, VDD, or VDDR first pacing mode to the DDI, DDIR, VVI, or VVIR second pacing mode, respectively, upon detecting a period of accelerated atrial arrhythmias based on information from the sensing circuitry, wherein the pacing controller is further operable to at least initially, upon switching from the first pacing mode to the second pacing mode, adjust the programmed lower pacing rate to an elevated adjusted lower rate, and further wherein the pacing controller is operable to decelerate the elevated adjusted lower rate towards a predetermined basic pacing rate that is as fast or faster than the programmed lower pacing rate during a deceleration period.

33. The device of claim 32, further wherein the pacing controller is operable to adjust the programmed lower pacing rate to an elevated adjusted lower rate based on R-R intervals measured during a ventricular response detection time window associated with switching from the first pacing mode to the second pacing mode.

34. The device of claim 33, wherein the pacing controller is further operable to:

measure one or more R-R intervals during the ventricular response detection time window based on information from the sensing circuitry;

determine at least the fastest R-R interval occurring during the ventricular response detection time window; and adjust the programmed lower pacing rate to the elevated adjusted lower rate based on at least the fastest R-R interval measured during the ventricular response detection time window.

35. The device of claim 32, further wherein the pacing controller is operable to:

determine the elevated adjusted lower rate based on R-R intervals measured during the ventricular response detection time window; and limit the elevated adjusted lower rate based on a programmed maximum pacing rate.

36. The device of claim 32, wherein the pacing controller is operable to switch from a DDDR or VDDR first pacing mode to a DDIR or VVIR second pacing mode, respectively, upon detection of a period of accelerated atrial arrhythmia, and further wherein the pacing controller is further operable to:

determine the elevated adjusted lower rate based on R-R intervals measured during a ventricular response detection time window;

compare the elevated adjusted lower rate to an activity sensor indicated pacing rate; and use either the elevated adjusted lower rate or the activity sensor indicated pacing rate based on the comparison.

37. The device of claim 32, wherein the pacing controller is further operable to readjust the elevated adjusted lower rate during the deceleration period based on intrinsic ventricular activity sensed by the sensing circuitry and control deceleration of the readjusted elevated lower rate during a reinitiated deceleration period.

38. The device of claim 32, further wherein the pacing controller is operable to continue deceleration towards the programmed basic pacing rate if no intrinsic ventricular activity is sensed during the deceleration period and thereafter continue use of the programmed basic pacing rate until either intrinsic ventricular activity is sensed and a new readjusted elevated lower rate is reset for deceleration during another deceleration period or operation is switched from the second pacing mode back to the first pacing mode.

39. The device of claim 32, wherein the pacing controller is further operable to switch from a DDDR or VDDR first pacing mode to a DDIR or VVIR second pacing mode, respectively, upon detection of a period of accelerated atrial arrhythmia, and further wherein the pacing controller is operable to:

compare the decelerating elevated adjusted lower rate to an activity sensor indicated pacing rate; and use either the decelerating elevated adjusted lower rate or the activity sensor indicated pacing rate based on the comparison.

40. The device of claim 32, wherein the implantable medical device comprises a bi-ventricular pacing apparatus, a dual chamber pacing apparatus, and a pacemaker/cardioverter/defibrillator.

* * * * *

UNITED STATES PATENT AND TRADEMARK OFFICE
CERTIFICATE OF CORRECTION

PATENT NO. : 6,477,420 B1 Page 1 of 1
APPLICATION NO. : 09/842879
DATED : November 5, 2002
INVENTOR(S) : Chester L. Struble et al.

It is certified that error appears in the above-identified patent and that said Letters Patent is hereby corrected as shown below:

Col 25, Line 13, delete "WIR second" and insert --WIR second--.

Signed and Sealed this

Twenty-fifth Day of July, 2006

JON W. DUDAS
*Director of the United States Patent and Trademark Office*